United States Patent [19]

Bernhart et al.

[11] Patent Number: 5,352,788
[45] Date of Patent: Oct. 4, 1994

[54] N-SUBSTITUTED HETEROCYCLIC DERIVATIVES

[75] Inventors: Claude Bernhart, Saint Gely du Fesc; Jean-Claude Breliere, Montpellier; Jacques Clement, Saussan; Dino Nisato, Saint Georges d'Orques; Pierre Perreault, Montpellier; Claude Muneaux; Yvette Muneaux, both of Les Matelles, all of France

[73] Assignee: Elf Sanofi, Paris, France

[21] Appl. No.: 79,866

[22] Filed: Jun. 23, 1993

Related U.S. Application Data

[62] Division of Ser. No. 794,497, Nov. 20, 1991, Pat. No. 5,270,317.

[30] Foreign Application Priority Data

| Mar. 30, 1990 | [FR] | France | 90 03563 |
| Aug. 8, 1990 | [FR] | France | 90 10144 |
| Sep. 10, 1991 | [FR] | France | 91 11161 |

[51] Int. Cl.$^5$ .............. C07D 239/36; C07D 233/70
[52] U.S. Cl. ................ 544/319; 544/6; 544/231; 540/543; 546/20; 548/300.7; 548/323.5; 548/324.1; 548/325.5; 548/316.4
[58] Field of Search ............ 544/6, 319, 231; 540/543; 546/20; 548/300.7, 323.5, 324.1, 325.5, 316.4

[56] References Cited

U.S. PATENT DOCUMENTS

| 4,355,040 | 10/1982 | Furukawa et al. | 424/273 |
| 4,614,535 | 9/1986 | Schmierer et al. | 71/92 |
| 4,880,804 | 11/1989 | Carini et al. | 514/234.5 |

FOREIGN PATENT DOCUMENTS

| 0103647 | 3/1984 | European Pat. Off. |
| 0226947 | 7/1987 | European Pat. Off. |
| 0253310 | 1/1988 | European Pat. Off. |
| 0291969 | 11/1988 | European Pat. Off. |
| 0323841 | 7/1989 | European Pat. Off. |
| 0324377 | 7/1989 | European Pat. Off. |
| 0411766 | 2/1991 | European Pat. Off. |
| 0412594 | 2/1991 | European Pat. Off. |

*Primary Examiner*—John M. Ford
*Attorney, Agent, or Firm*—Bacon & Thomas

[57] ABSTRACT

The invention relates to processes for preparing N-substituted heterocyclic compounds of formula (I)

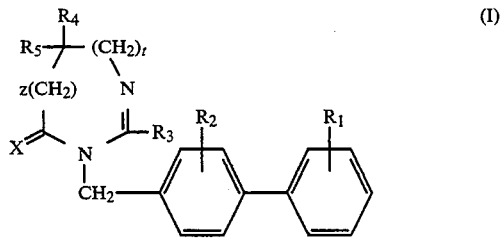

wherein the substituents are as described in the specification, and to intermediates. The compounds are useful for antagonizing angiotensin II.

16 Claims, No Drawings

N-SUBSTITUTED HETEROCYCLIC DERIVATIVES

The present application is a divisional application of U.S. Ser. No. 07/794,497, filed Nov. 20, 1991, now U.S. Pat. No. 5,270,317, which is a continuation-in-part of International Application Serial No. PCT/FR91/00224, filed Mar. 20, 1991.

The present invention relates to N-substituted heterocyclic derivatives, to their preparation and to the pharmaceutical compositions in which they are present.

The compounds according to the invention antagonize the action of angiotensin II, which is a peptide hormone of the formula

H-Asp-Arg-Val-Tyr-Ile-His-Pro-Phe-OH

Angiotensin II is a potent vasopressor and the biologically active product of the renin-angiotensin system: renin acts on the angiotensinogen of the plasma to produce angiotensin I, which is converted to angiotensin II by the action of the angiotensin I converting enzyme.

The compounds of the present invention are nonpeptide compounds which antagonize angiotensin II. By inhibiting the action of angiotensin II on its receptors, the compounds according to the invention prevent especially the increase in blood pressure produced by the hormone-receptor interaction; they also have other physiological actions on the central nervous system and on the kidneys, for example.

Thus the compounds according to the invention are useful in the treatment of cardiovascular complaints such as hypertension and heart failure, as well as in the treatment of complaints of the central nervous system and in the treatment of glaucoma, diabetic retinopathy and renal insufficiency.

The present invention relates to compounds of the formula

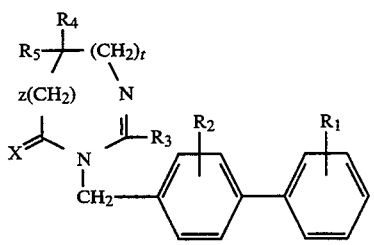

(I)

in which:

R$_1$ and R$_2$ are similar or different and are each independently hydrogen or a group selected from a C$_1$-C$_6$ alkyl, a C$_1$-C$_4$ alkoxy, an amino, an aminomethyl, a carboxyl, an alkoxycarbonyl in which the alkoxy is C$_1$-C$_4$, a cyano, a tetrazolyl, a methyltetrazolyl, a methylsulfonylamino, a trifluoromethylsulfonylamino, a trifluoromethylsulfonylaminomethyl, an N-cyanoacetamide, an N-hydroxyacetamide, an N-(4-carboxy-1,3-thiazol-2-yl)acetamide, a ureido, a 2-cyanoguanidinocarbonyl, a 2-cyanoguanidinomethyl, an imidazol-1-ylcarbonyl, and a 3-cyano-2-methylisothioureidomethyl, with the proviso that at least one of the substituents R$_1$ or R$_2$ is other than hydrogen;

R$_3$ is a hydrogen, a C$_1$-C$_6$ alkyl which is unsubstituted or substituted by one or more halogen atoms, a C$_2$-C$_6$ alkenyl, a C$_3$-C$_7$ cycloalkyl, a phenyl, a phenylalkyl in which the alkyl is C$_1$-C$_3$, or a phenylalkenyl in which the alkenyl is C$_2$-C$_3$, said phenyl groups being unsubstituted or monosubstituted or polysubstituted by a halogen atom, a C$_1$-C$_4$ alkyl, a C$_1$-C$_4$ halogenoalkyl, a C$_1$-C$_4$ polyhalogenoalkyl, a hydroxyl or a C$_1$-C$_4$ alkoxy; and either R$_4$ and R$_5$ are each independently a C$_1$-C$_6$ alkyl, a phenyl or a phenylalkyl in which the alkyl is C$_1$-C$_3$, said alkyl, phenyl and phenylalkyl groups being unsubstituted or substituted by one or more halogen atoms or by a group selected from a C$_1$-C$_4$ perfluoroalkyl, a hydroxyl and a C$_1$-C$_4$ alkoxy;

or R$_4$ and R$_5$ together form a group of the formula =CR$_7$R$_8$, in which R$_7$ is hydrogen, a C$_1$-C$_4$ alkyl or a phenyl and R$_8$ is a C$_1$-C$_4$ alkyl or a phenyl;

or else R$_4$ and R$_5$ together are either a group of the formula (CH$_2$)$_n$ or a group of the formula (CH$_2$)$_p$Y(CH$_2$)$_q$, in which Y is either an oxygen atom, or a sulfur atom, or a carbon atom substituted by a C$_1$-C$_4$ alkyl group, a phenyl or a phenylalkyl in which the alkyl is C$_1$-C$_3$, or a group N—R$_6$, in which R$_6$ is a hydrogen, a C$_1$-C$_4$ alkyl, a phenylalkyl in which the alkyl is C$_1$-C$_3$, a C$_1$-C$_4$ alkylcarbonyl, a C$_1$-C$_4$ halogenoalkylcarbonyl, a C$_1$-C$_4$ polyhalogenoalkylcarbonyl, a benzoyl, an alpha-aminoacyl or an N-protecting group, or R$_4$ and R$_5$, together with the carbon atom to which they are bonded, form an indane or an adamantane;

p+q=m;

n is an integer between 2 and 11; and m is an integer between 2 and 5; or

R$_4$ is a C$_1$-C$_6$ alkyl which is unsubstituted or substituted by one or more halogen atoms; and R$_5$ is a cycloalkyl or a cycloalkylmethyl, said cycloalkyl being C$_3$-C$_7$, which is unsubstituted or substituted by one or more halogen atoms;

or R$_4$ and R$_5$ are each a cyclopropyl;

X is an oxygen atom or sulfur atom; and z and t are zero or one is zero and the other is one; and their salts.

If a compound according to the invention has an asymmetric carbon, the invention includes each of the 2 optical isomers of this compound and their racemic mixture.

The salts of the compounds of formula (I) according to the present invention include those with mineral or organic acids which permit separation or suitable crystallization of the compounds of formula (I), such as trifluoroacetic acid, picric acid, oxalic acid or an optically active acid, for example a mandelic acid or a camphosulfonic acid, and acids which form pharmaceutically acceptable salts such as the hydrochloride, the hydrobromide, the sulfate, the hydrogensulfate, the dihydrogenphosphate, the methanesulfonate, the methylsulfate, the maleate, the fumarate and the naphthalene-2-sulfonate.

The salts of the compounds of formula (I) also include the salts with organic or mineral bases, for example the salts of alkali or alkaline earth metals, such as the sodium, potassium and calcium salts, the sodium and potassium salts being preferred, or with a tertiary amine such as trometamol, or else the salts of arginine, lysine or any physiologically acceptable amine.

According to the present description and in the claims which follow, halogen atom is understood as meaning a bromine, chlorine or fluorine atom; N- protecting group (also designated by Pr) is understood as meaning a group conventionally used in peptide chemistry for affording temporary protection of the amine group, for example a Boc, Z or Fmoc group or a benzyl group; esterified carboxyl group is understood as meaning an ester which is labile under appropriate conditions, such as, for example, a methyl, ethyl, benzyl or tert-butyl ester. "Alkyl" denotes linear or branched saturated aliphatic hydrocarbon radicals.

The compounds of formula (I) in which $R_1$ is in the ortho position and is a carboxyl or tetrazolyl group and $R_2$ is hydrogen are preferred compounds.

The compounds of formula (I) in which $R_4$ and $R_5$ together form, with the carbon to which they are bonded, a cyclopentane or a cyclohexane are preferred compounds.

The compounds of formula (I) in which $R_4$ is methyl and $R_5$ is cyclohexyl are also preferred compounds.

Likewise, the compounds of formula (I) in which $R_3$ is a liner $C_1$-$C_6$ alkyl group art preferred compounds.

The compounds of formula (I) in which X is an oxygen atom are also preferred compounds.

Finally, the compounds of formula (I) in which $z=t=0$ are preferred compounds.

2-n-Butyl-4-methyl-4-cyclohexyl-1-[(2'-(tetrazol-5-yl)biphenyl-4-yl)methyl]-2-imidazolin-5-one and 2-n-butyl-4-spirocyclopentane-1-[(2'-(tetrazol-5-yl)biphenyl-4-yl)methyl]-2-imidazolin-5-one or one of their salts with acids or bases are particularly preferred.

The following abbreviations are used in the description and in the Examples:
alcohol: ethyl alcohol
Et: ethyl
dry ice: solid carbon dioxide
nBu, tBu: n-butyl, tert-butyl
DMF: dimethylformamide
THF: tetrahydrofuran
DCM: dichloromethane
NBS: N-bromosuccinimide
DCC: dicyclohexylcarbodiimide
DIPEA: diisopropylethylamine
ether: ethyl ether
TFA: trifluoroacetic acid
Z: benzyloxycarbonyl
Boc: tert-butoxycarbonyl
BOP: benzotriazolyloxytrisdimethylaminophosphonium hexafluorophosphate
Fmoc: fluorenylmethoxycarbonyl The present invention further relates to the method of preparing the compounds (I). In said method:

a1) a heterocyclic derivative of the formula

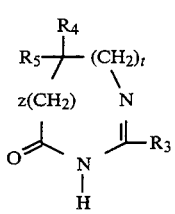

in which z, t, $R_3$, $R_4$ and $R_5$ are as defined above for (I), is reacted with a (biphenyl-4-yl)methyl derivative of the formula

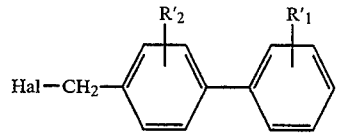

in which Hal is a halogen atom and $R'_1$ and $R'_2$ are respectively either $R_1$ and $R_2$ or a precursor group of $R_1$ and $R_2$;

b1) if appropriate, the resulting compound of the formula

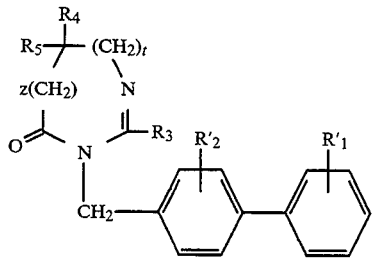

is treated with Lawesson's reagent [2,4-bis(4-methoxyphenyl)-1,3-dithia-2,4-diphosphetane 2,4-disulfide]; and c1) the compound obtained in a1) or b1), of the formula

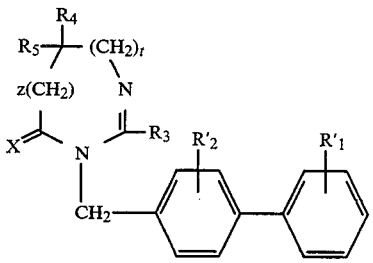

in which X is an oxygen atom or a sulfur atom, is treated to give the compound (I) by conversion of the groups $R'_1$ and/or $R'_2$ to the groups $R_1$ and/or $R_2$ respectively.

Among the compounds 2, the compounds (II) as defined below are novel.

Thus the present invention further relates to the compounds (II) of the formula

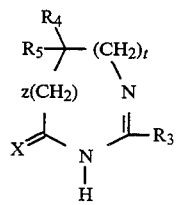

in which:
X is an oxygen atom or sulfur atom;
z and t are zero or one is zero and the other is one;
$R_3$ is a hydrogen, a $C_1$-$C_6$ alkyl which is unsubstituted or substituted by one or more halogen atoms, a $C_2$-$C_6$ alkenyl, a $C_3$-$C_7$ cycloalkyl, a phenyl, a phenylalkyl in which the alkyl is $C_1$-$C_3$, or a phenylalkenyl in which the alkenyl is $C_2$-$C_3$, said phenyl groups being unsubstituted or monosubstituted or polysubstituted by a halogen atom, a $C_1$-$C_4$ alkyl, a $C_1$-$C_4$ halogenoalkyl, a $C_1$-$C_4$ polyhalogenoalkyl, a hydroxyl or a $C_1$-$C_4$ alkoxy; and either

- $R_4$ and $R_5$ are each independently a $C_1$-$C_6$ alkyl, a phenyl or a phenylalkyl in which the alkyl is $C_1$-$C_3$, said alkyl, phenyl and phenylalkyl groups being unsubstituted or substituted by one or more halogen atoms or by a group selected from a $C_1$-$C_4$ perfluoroalkyl, a hydroxyl and a $C_1$-$C_4$ alkoxy;
- or $R_4$ and $R_5$ together form a group of the formula $=CR_7R_8$, in which $R_7$ is hydrogen, a $C_1$-$C_4$ alkyl or a phenyl and $R_8$ is a $C_1$-$C_4$ alkyl or a phenyl;
- or else $R_4$ and $R_5$ together are either a group of the formula $(CH_2)_n$ or a group of the formula $(CH_2)_p Y(CH_2)_q$, in which Y is either an oxygen atom, or a sulfur atom, or a carbon atom substituted by a $C_1$-$C_4$ alkyl group, a phenyl or a phenylalkyl in which the alkyl is $C_1$-$C_3$, or a group N—$R_6$, in which $R_6$ is a hydrogen, a $C_1$-$C_4$ alkyl, a phenylalkyl in which the alkyl is $C_1$-$C_3$, a $C_1$-$C_4$ alkylcarbonyl, a $C_1$-$C_4$ halogenoalkylcarbonyl, a $C_1$-$C_4$ polyhalogenoalkylcarbonyl, a benzoyl, an alpha-aminoacyl or an N-protecting group, or $R_4$ and $R_5$, together with the carbon atom to which they are bonded, form an indane or an adamantane;

$p+q=m$;

n is an integer between 2 and 11; and m is an integer between 2 and 5;

with the limitation that if z and t are zero and X is an oxygen atom, $R_4$ and $R_5$ are other than
- a $C_1$-$C_6$ alkyl, a phenyl or a phenylalkyl in which the alkyl is $C_1$-$C_3$, said alkyl, phenyl and phenylalkyl groups being unsubstituted or substituted by one or more halogen atoms or by a group selected from a $C_1$-$C_4$ perfluoroalkyl, a hydroxyl and a $C_1$-$C_4$ alkoxy;
- or $R_4$ and $R_5$ together are other than a group N—$R_6$ in which $R_6$ is a hydrogen, a $C_1$-$C_4$ alkyl or a phenylalkyl in which the alkyl is $C_1$-$C_3$; and
- n is other than 6; or when $R_3$ represents a substituted phenyl group, $R_4$ and $R_5$ together are other than a $(CH_2)_n$ group in which n is between 3 and 5;

and if $z=1$ and $R_3$ is a phenyl, $R_4$ and $R_5$ are each other than a methyl; or

- $R_4$ is a $C_1$-$C_6$ alkyl which is unsubstituted or substituted by one or more halogen atoms; and
- $R_5$ is a cycloalkyl or a cycloalkylmethyl, the cycloalkyl being $C_3$-$C_7$, which is unsubstituted or substituted by one or more halogen atoms;
- or else $R_4$ and $R_5$ are each a cyclopropyl.

Among the derivatives (II), the compounds in which $z=t=0$, of the formula

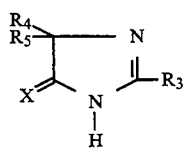

(II')

in which X, $R_3$, $R_4$ and $R_5$ are as defined above for (II), are preferred compounds.

Particularly preferred compounds of formula (II') are those in which $R_4$ and $R_5$ form a cyclopentane together with the carbon to which they are bonded, and those in which $R_4$ is a methyl and $R_5$ is a cyclohexyl. These compounds have the formula

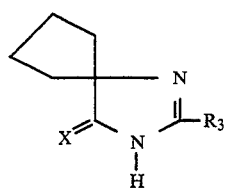

(II'$_a$)

or

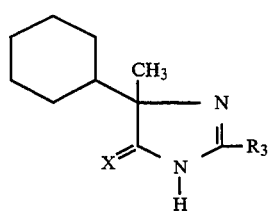

(II'$_b$)

in which $R_3$ and X are as defined above. If X is an oxygen atom, $R_3$ is other than a substituted phenyl group for the compound (II'$_a$).

The compounds (II) in which $z=0$ and $t=1$, of the formula

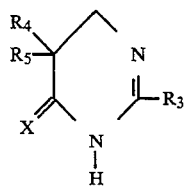

(II'')

in which $R_3$, $R_4$, $R_5$ and X are as defined above for (II), are preferred compounds.

Finally, the compounds (II) in which $z=1$ and $t=0$, of the formula

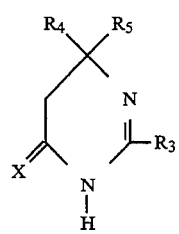

(II''')

in which:

$R_3$ is a hydrogen, a $C_1$-$C_6$ alkyl which is unsubstituted or substituted by one or more halogen atoms, a $C_2$-$C_6$ alkenyl, a $C_3$-$C_7$ cycloalkyl, a phenyl, a phenylalkyl in which the alkyl is $C_1$-$C_3$, or a phenylalkenyl in which the alkenyl is $C_2$-$C_3$, said phenyl groups being unsubstituted or monosubstituted or polysubstituted by a halogen atom, a $C_1$-$C_4$ alkyl, a $C_1$-$C_4$ halogenoalkyl, a $C_1$-$C_4$ polyhalogenoalkyl, a hydroxyl or a $C_1$-$C_4$ alkoxy; and either $R_4$ and $R_5$ are each independently a $C_1$-$C_6$ alkyl, a phenyl or a phenylalkyl in which the alkyl is $C_1$–$C_3$, said alkyl, phenyl and phenylalkyl groups being unsubstituted or substituted by one or more halogen atoms or by a group selected from a $C_1$–$C_4$ perfluoroalkyl, a hydroxyl and a $C_1$–$C_4$ alkoxy;

or $R_4$ and $R_5$ together form a group of the formula =$CR_7R_8$, in which $R_7$ is hydrogen, a $C_1$–$C_4$ alkyl or a phenyl and $R_8$ is a $C_1$–$C_4$ alkyl or a phenyl;

or $R_4$ and $R_5$ together are either a group of the formula $(CH_2)_n$ or a group of the formula $(CH_2)_pY(CH_2)_q$, in which Y is either an oxygen atom, or a sulfur atom, or a carbon atom substituted by a $C_1$–$C_4$ alkyl group, a phenyl or a phenylalkyl in which the alkyl is $C_1$–$C_3$, or a group N—$R_6$, in which $R_6$ is a hydrogen, a $C_1$–$C_4$ alkyl, a phenylalkyl in which the alkyl is $C_1$–$C_4$, a $C_1$–$C_4$ alkylcarbonyl, a $C_1$–$C_4$ halogenoalkylcarbonyl, a $C_1$–$C_4$ polyhalogenoalkylcarbonyl, a benzoyl, an alpha-aminoacyl or an N-protecting group, or $R_4$ and $R_5$, together with the carbon atom to which they are bonded, form an indane or an adamantane;

$p+q=m$;

n is an integer between 2 and 11; and m is an integer between 2 and 5; or $R_4$ is a $C_1$–$C_6$ alkyl which is unsubstituted or substituted by one or more halogen atoms; and $R_5$ is a cycloalkyl or a cycloalkylmethyl, the cycloalkyl being $C_3$–$C_7$, which is unsubstituted or substituted by one or more halogen atoms;

or else $R_4$ and $R_5$ are each a cyclopropyl; and

X is an oxygen atom or a sulfur atom; with the limitation that $R_3$ is other than a phenyl if $R_4$ and $R_5$ are each a methyl, are preferred compounds.

The derivatives 2 are prepared by known methods. For example, it is possible to use the method described by Jacquier et al. (Bull. Soc. Chim. France, 1971, 3, 1040-1051) and by Brunken and Bach (Chem. Ber., 1956, 89, 1363-1373) and to react an alkyl imidate with an amino acid or its ester in accordance with the following reaction scheme:

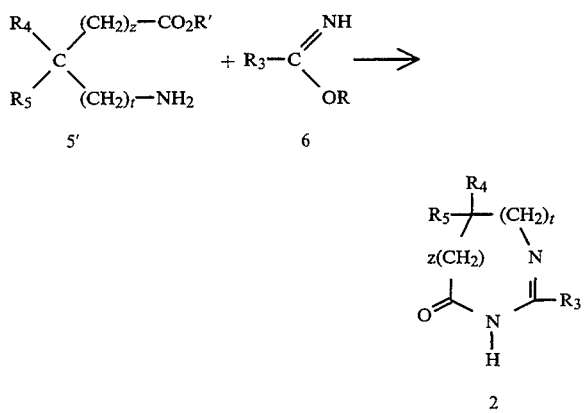

in which R is a $C_1$–$C_4$ alkyl, R' is hydrogen or a $C_1$–$C_4$ alkyl and $R_3$, $R_4$, $R_5$, z and t are as defined above for (I).

This reaction is carried out in an acid medium by heating in an inert solvent such as xylene or toluene.

The compounds 5' are known compounds or are prepared by known methods. The compounds 5' can be obtained optically pure using methods of asymmetric synthesis or methods of resolving the racemic mixture, such as those described in "Synthesis of Optically Active Alpha-aminoacids, R. M. Williams, Pergamon Press, 1989".

According to another procedure, the compound 2 can be prepared by reacting an aminoalkylamide (5″) with an alkyl ortho-ester (10) in an acid medium in accordance with the following reaction scheme:

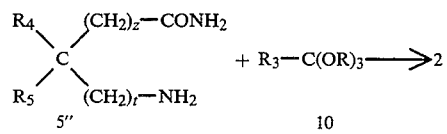

in which R is a $C_1$–$C_4$ alkyl.

Using a procedure described by H. Takenaka et al. (Heterocycles, 1989, 29(6), 1185-89), it is also possible to prepare the compound 2 by reacting an acid halide of the formula $$R_3\text{—CO—Hal} \qquad 12$$

in which Hal is a halogen, preferably chlorine, with the derivative 5″; the cyclization of the diamide is then carried out in a basic medium.

If $z=t=0$, a derivative 5″ can be prepared from a ketone by a procedure described in U.S. Pat. No. 4,017,510 or in Swiss patent 540 271:

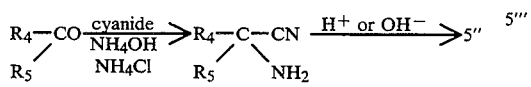

The ketone $R_4R_5CO$ is treated with cyanide (hydrocyanic acid, sodium cyanide or potassium cyanide) and ammonium ions (aqueous ammonia and ammonium chloride); the aminonitrile compound 5‴ is then hydrolyzed to 5″, either in a strongly acidic medium or in a basic medium. If appropriate, the aminonitrile 5‴ can be resolved with an optically active acid by the procedure in European patent 158 000, in which case it is possible to prepare the compound 5' and then the compound 2 in optically pure form.

More particularly, according to another object of the present invention, the compound 2 is prepared by a method which comprises reacting a compound of the formula $$R_3\text{—T} \qquad 14$$

in which T is a group $C(OR)_3$ a group

or a group COHal

R being a $C_1$–$C_4$ alkyl and Hal denoting a halogen atom, preferably chlorine, with a compound of the formula $$\begin{array}{c} R_4 \diagdown \diagup (CH_2)_z COA \\ \diagup \diagdown \\ R_5 \quad (CH_2)_t NH_2 \end{array} \qquad 13$$

in which A is an OH group, an NH₂ group or a group OR', R' being hydrogen or a C₁–C₄ alkyl, and then, if appropriate, treating the resulting compound with Lawesson's reagent (2,4-bis(4-methoxyphenyl)-1,3-dithia-2,4-diphosphetane disulfide).

The (biphenyl-4-yl)methyl derivative (3) is prepared by a method described in European patent application 324 377.

The conversion of a group R'₁ and/or R'₂ to a group R₁ and/or R₂ is effected by methods well known to those skilled in the art. Thus, if the compound (I) to be prepared possesses a group R₁ and/or R₂=carboxyl, R'₁ and/or R'₂ are an esterified carboxyl group. If the compound (I) to be prepared possesses a group R₁ and/or R₂=tetrazolyl, R'₁ and/or R'₂ can be either a tetrazolyl protected for example by a trityl group, or a cyano group which will subsequently be replaced with a tetrazolyl group protected if necessary by a trityl. The conversion of the cyano group to a tetrazolyl can be effected with an azide, for example tributyltin azide or sodium azide.

It is also possible to use groups R'₁ and/or R'₂ such as nitro, carboxyl, cyano or acid chloride groups and then to convert them by reactions well known to those skilled in the art to give groups R₁ and/or R₂ as defined for the compound (I).

Thus, if R'₁ and/or R'₂ are a carboxyl, they can be converted to R₁ and/or R₂ in the form of an imidazol-1-ylcarbonyl or else an N-(4-carboxy-1,3-thiazol-2-yl)acetamide.

The group R'₁ and/or R'₂ in the form of an acid chloride can be converted to R₁ and/or R₂ in the form of N-hydroxyacetamide, N-cyanoacetamide, ureido or 2-cyanoguanidinocarbonyl.

The group R'₁ and/or R'₂ in the form of a nitro can be converted to amino, from which R₁ and/or R·is prepared in the form of methylsulfonylamino, trifluoromethylsulfonylamino or trifluoromethylsulfonylaminomethyl.

The group R'₁ and/or R'₂ in the form of a cyano can be converted to aminomethyl, from which a 3-cyano-2-methylisothioureidomethyl is prepared (according to C. Gordon et al., J. Org. Chem., 1970, 35(6), 2067–2069) or a 2-cyanoguanidinomethyl is prepared (according to R. W. Turner, Synthesis, 1975, 332).

Step a1) is carried out in an inert solvent such as DMF, DMSO or THF, in a basic medium, for example in the presence of potassium hydroxide, a metal alcoholate, a metal hydride, calcium carbonate or tri-ethylamine.

Step b1) is carried out by heating under nitrogen in a solvent such as toluene, according to the method described by M. P. Cava et al., Tetrahedron, 1985, 41, 22, 5061.

In the description below, the method comprising steps a1, b1 and c1 is referred to as method 1.

Alternatively, the compounds (I) can be prepared by another method, which is also a subject of the present invention. In this method:

a2) an amino acid of the formula $$\begin{array}{c} R_4 \diagdown \diagup (CH_2)_t-NHPr \\ C \\ \diagup \diagdown \\ R_5 \quad (CH_2)_z \\ \mid \\ COOH \end{array} \qquad 7$$

in which z, t, R₄ and R₅ are as defined above for (I), and of which the amine group is protected by the Pr group, is reacted with a (biphenyl-4-yl)methylamine derivative of the formula $$H_2N-CH_2-\underset{R'_2}{\underset{|}{\bigodot}}-\underset{R'_1}{\underset{|}{\bigodot}} \qquad 8$$

in which R'₁ and R'₂ are respectively either R₁ and R₂ or a precursor group of R₁ and R₂;

b2) after deprotection of the amine, the resulting compound of the formula $$\begin{array}{c} R_4 \diagdown \qquad\qquad O \\ \diagup C-(CH_2)_z-\overset{\|}{C}-NH-CH_2-\underset{R'_2}{\underset{|}{\bigodot}}-\underset{R'_1}{\underset{|}{\bigodot}} \\ R_5 \quad (CH_2)_t-NH_2 \end{array} \qquad 9$$

is then treated with an alkyl ortho-ester of the formula R₃C(OR)₃ (10), in which R₃ is as defined above for (I) and R is a C₁–C₄ alkyl;

c2) if appropriate, the resulting compound of the formula

4 is treated with Lawesson's reagent [2,4-bis(4-methoxyphenyl)-1,3-dithia-2,4-diphosphetane 2,4-disulfide]; and d2) the compound thus obtained in b2 or c2, of the formula

5 is then treated under suitable conditions for preparing the compound (I) by conversion of the groups R'₂ and/or R'₁ to the groups R₂ and/or R₁ respectively.

The compounds 7 are known or are prepared by known methods (Chemistry of the Amino Acids, Greenstein and Winitz, published by John Wiley, 1961, vol. I, p. 697). If appropriate, these compounds can be obtained optically pure using methods of asymmetric synthesis or methods of resolving the racemic mixture, such as those described in "Synthesis of Optically Active Alphaaminoacids, R. M. Williams, Pergamon Press, 1989".

The compounds 8 are prepared according to European patent application 324 377. Step a2) is carried out under the usual conditions for the coupling of an acid with an amine, for example in the presence of BOP and DIPEA.

Step b2), which is the cyclization of the compound 9 in the presence of 10, is carried out according to Jacquier et al. (Bull. Soc. Chim. France, 1971, (3), 1040–1051) and according to Brunken and Bach (Chem. Bet., 1956, 89, 1363–1373).

In the description below, the method comprising steps a2 to d2 is referred to as method 2.

In one variant of method 2, in step b2, it is possible, if appropriate, to isolate an intermediate 9' of the formula

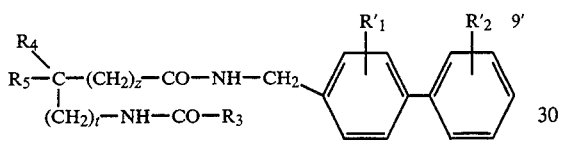

and then to prepare the compound 4 by cyclization in an acid medium.

In another variant of method 2, in order to prepare a compound (I) in which $R_4R_5$ is a group $=CR_7R_8$, an amino acid of the formula

can be reacted in an acid medium with an aldehyde or a ketone of the formula $$R_7COR_8$$

in which $R_7$ and $R_8$ are as defined above for (I), and the product is then reacted with the compound 8 to give a compound of the formula

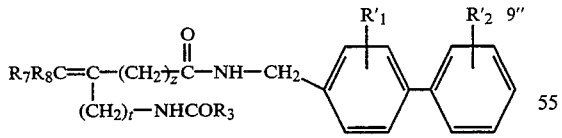

The cyclization of this compound in an acid medium leads to the compound 4.

In this method, to prepare a compound (I) in which $R_1$ and/or $R_2$ are a carboxyl group, the substituents $R'_1$ and/or $R'_2$ are preferably a tert-butoxycarbonyl group.

Finally, another alternative for the preparation of the compounds (I) according to the invention in which z and t are equal to zero and $R_5$ is other than a cycloalkyl or a cycloalkylmethyl wherein the cycloalkyl is a $C_3-C_7$ cycloalkyl, is the photooxidation method, which is also a subject of the present invention.

In this last method:

a3) a (biphenyl-4-yl)methyl derivative of the formula

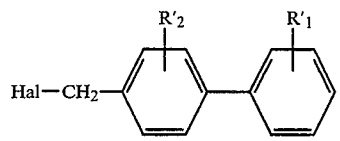

in which Hal is a halogen atom and $R'_1$ and $R'_2$ are respectively either $R_1$ and $R_2$ or a precursor group of $R_1$ and $R_2$, is reacted with an imidazole derivative of the formula

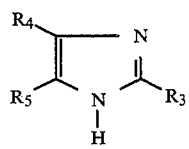

in which $R_3$, $R_4$ and $R_5$ are as defined above for (I), in the presence of oxygen and UV irradiation and in a basic medium;

b3) if appropriate, the resulting compound of the formula

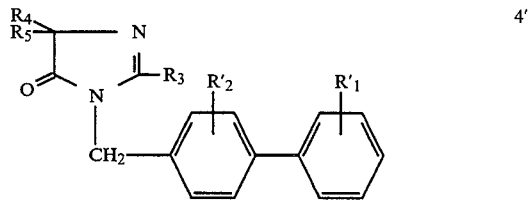

is treated with Lawesson's reagent [2,4-bis(4-methoxyphenyl)-1,3-dithia-2,4-diphosphetane 2,4-disulfide]; and c3) the compound thus obtained in b3 or c3, of the formula

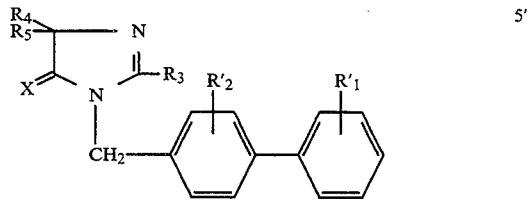

is then treated under suitable conditions for preparing the compound (I) by conversion of the groups $R'_1$ and/or $R'_2$ to the groups $R_1$ and/or $R_2$ respectively.

The imidazole derivative 11 is either commercially available, or known, or is prepared by known methods indicated above for the preparation of the compounds 2.

Step a3) is carried out in an inert solvent such as, for example, DMF; to facilitate the reaction, a photosensitizing product such as methylene blue can be added.

In the description below, the method comprising steps a3) to c3) is referred to as method 3.

The compounds (I) according to the invention in which $R_4$ and $R_5$ together are a group of the formula $(CH_2)_pY(CH_2)_q$ in which Y is an NH group can be prepared by catalytic hydrogenolysis of a corresponding compound (I) in which Y is a group N—R$_6$, R$_6$ being a benzyl.

The affinity of the products according to the invention for angiotensin II receptors was studied in a test for the binding of angiotensin II, labeled with iodine 125, to rat liver membrane receptors. The method used is the one described by S. KEPPENS et al. in Biochem. J., 1982, 208, 809–817.

The IC$_{50}$, namely the concentration which gives a 50% displacement of the labeled angiotensin II bound specifically to the receptor is measured The IC$_{50}$ of the compounds according to the invention is less than $10^{-6}$M.

Also, the effect of the products according to the invention as angiotensin II antagonists was observed on different animal species in which the reninangiotensin system had been activated beforehand (C. LACOUR et al., J. Hypertension, 1989, 7 (suppl. 2), S33–S35).

The compounds according to the invention are active after administration by different routes, especially after oral administration.

No signs of toxicity are observed with these compounds at the pharmacologically active doses.

Thus the compounds according to the invention can be used in the treatment of various cardiovascular complaints, especially hypertension, heart failure and venous insufficiency, as well as in the treatment of glaucoma, diabetic retinopathy and various complaints of the central nervous system, for example anxiety, depression, memory deficiencies or Alzheimer's disease.

The present invention further relates to pharmaceutical compositions containing an effective dose of a compound according to the invention, or of a pharmaceutically acceptable salt, and suitable excipients. Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula I above, or their salts if appropriate, can be administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To achieve the desired prophylactic or therapeutic effect, the dose of active principle can vary between 0.01 and 50 mg per kg of body weight per day.

Each unit dose can contain from 0.1 to 1000 mg, preferably 1 to 500 mg, of active ingredients in combination with a pharmaceutical carrier. This unit dose can be administered 1 to 5 times a day so as to administer a daily dosage of 0.5 to 5000 mg, preferably 1 to 2500 mg.

When a solid composition in the form of tablets is prepared, the main active ingredient is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a prolonged or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir or for administration in the form of drops can contain the active ingredient in conjunction with a sweetener, which is preferably calorie-free, methylparaben and propylparaben as antiseptics, as well as a flavoring and an appropriate color.

The water-dispersible granules or powders can contain the active ingredient mixed with dispersants or wetting agents, or suspending agents such as polyvinylpyrrolidone, as well as with sweeteners or taste correctors.

Rectal administration is effected using suppositories prepared with binders which melt at the rectal temperature, for example cacao butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, with one or more carriers or additives if appropriate.

In addition to the products of formula I above or one of the pharmaceutically acceptable salts, the compositions of the present invention can contain other active principles such as, for example, tranquilizers or other drugs which can be useful in the treatment of the disorders or diseases indicated above.

Thus the present invention relates to pharmaceutical compositions containing several active principles in association, one being a compound according to the invention and it being possible for the other or others to be a beta-blocking compound, a calcium antagonist, a diuretic, a non-steroidal antiinflammatory or a tranquilizer.

The following Examples illustrate the invention without however implying a limitation. The following abbreviations are used in these Examples: d denotes density, RT denotes room temperature, KHSO$_4$—K$_2$SO$_4$ denotes an aqueous solution containing 16.6 g of potassium bisulfate and 33.3 g of potassium sulfate per liter.

The melting points (m.p.) are given in degrees Celsius; unless indicated otherwise, they were measured without recrystallization of the product.

The purity of the products is checked by thin layer chromatography (TLC) or HPLC. The products are characterized by their NMR spectra run at 200 MHz in deuterated DMSO with tetramethylsilane as the internal reference.

The specific optical rotations ($[\alpha]_D$) are measured at 22° C.:

path length: 10 cm, concentration: 1 g per 100 ml.

The following abbreviations are used in the interpretation of the NMR spectra:

s: singlet sb: broad singlet d: doublet t: triplet q: quadruplet quint: quintuplet sext: sextuplet
m: unresolved signals or multiplet
In addition, im denotes imidazole.
Conventionally, the hydrogen atoms are numbered on the biphenylyl as shown in the following formula:

$$\text{(I)}$$

In the following compounds, z and t are zero except where the compound prepared is a pyrimidinone.

EXAMPLE 1

2-n-Butyl-4-spirocyclopentane-1-[(2'-tert-butoxycarbonylbiphenyl-4-yl)methyl]-2-imidazolin-5-one and 2-n-butyl-1-[(2'-carboxybiphenyl-4-yl)methyl]-4-spirocyclopentane-2-imidazolin-5-one trifluoroacetate

Method 2

A) 1-N-Fmoc-aminocyclopentanecarboxylic acid is prepared according to the method described by CHI-DEU CHANG et al. (Int. J. Peptide Protein Res., 1980, 15, 59–66). M.p.=89°–91° C.

B) N-(2'-Tert-butoxycarbonylbiphenyl-4-ylmethyl)-1-(N-Fmoc-amino)cyclopentane-1-carboxamide 700 mg of the product prepared in the previous step are dissolved in 8 ml of DMF, and 576 mg of 4-aminomethyl-2'-tert-butoxycarbonylbiphenyl, 970 mg of BOP and a sufficient amount of DIPEA to bring the pH to 6 are added successively.

After stirring for 1 hour, the reaction medium is diluted with 100 ml of ethyl acetate and 20 ml of water; the organic phase is washed successively with a saturated solution of sodium bicarbonate, then with a $KHSO_4$—$K_2SO_4$ solution and finally with a saturated solution of sodium chloride. After drying over sodium sulfate, the solution is evaporated to dryness to give an oil.

m=1.2 g.

C) N-(2'-Tert-butoxycarbonylbiphenyl-4-ylmethyl)-1-aminocyclopentane-1-carboxamide The product obtained in the previous step is dissolved in 10 ml of DMF, 1 ml of diethylamine is then added and the mixture is stirred for 1 hour 15 minutes at RT. The reaction medium is taken up in 100 ml of ethyl acetate and 20 ml of water and the organic phase is then washed once with water and once with a saturated solution of sodium chloride and then dried over sodium sulfate and evaporated to dryness.

The residue is chromatographed on silica gel using an ethyl acetate/methanol/30% aqueous ammonia mixture (99/1/0.5; v/v/v) as the eluent to give 600 mg of the expected product.

IR (CHCl$_3$): 3350 cm$^{-1}$: H (amide and amine) 1700 cm$^{-1}$: C=O (CO$_2$tBu) 1650 cm$^{-1}$: C=O (CONH) NMR spectrum: 1.25 ppm: s: 9H: tBu 2.15–1.40 ppm: m: 10H: C$_5$H$_8$, NH$_2$ 4.40 ppm: d: 2H: C$\underline{H}_2$—NH 7.15–7.75 ppm: m: 8H: biphenyl 8.60 ppm: t: 1$\underline{H}$: N$\underline{H}$—CH$_2$ D) 2-n-Butyl-4-spirocyclopentane-1-[(2'-tert-butoxycarbonylbiphenyl-4-yl)methyl]-2-imidazolin-5-one 394 mg of the product prepared in the previous step and 250 mg of ethyl orthovalerate are mixed in 2 ml of DCM. 1 drop of acetic acid is added and the mixture is then heated at 90° C. with the DCM being allowed to evaporate off. After 1 hour 15 minutes, the reaction medium is taken up in 50 ml of ethyl acetate, 10 ml of water and 1 ml of a saturated solution of sodium bicarbonate. The organic phase is then washed with a saturated solution of sodium chloride and subsequently dried over sodium sulfate and evaporated to dryness. The residue is chromatographed on silica gel using an ethyl acetate/toluene mixture (½; v/v) as the eluent to give 390 mg of the expected product, which crystallizes.

M.p.=63°–65° C. IR (CHCl$_3$): 1710–1720 cm$^{-1}$; C=O, C=O (ester and imidazoline) 1625 cm$^{-1}$: C=N NMR spectrum: 0.88 ppm: t: 3H: CH$_3$ (nBu) 1.20 ppm: s: 9H: tBu 1.35 ppm: sext: 2H: CH$_3$—C$\underline{H}_2$— 1.58 ppm: quint: 2H: CH$_3$—CH$_2$—C$\underline{H}_2$— 1.95–1.65 ppm: m: 8H: cyclopentane 2.42 ppm: t: 2H: CH$_3$—CH$_2$—CH$_2$—C$\underline{H}_2$— 4.78 ppm: s: 2H: C$\underline{H}_2$—C$_6$H$_4$— 7.20–7.80 ppm: m: 8H: aromatic protons Mass spectrum: MH$^+$; 461

E) 2-n-Butyl-1-[(2'-carboxybiphenyl-4-yl)methyl]-4-spirocyclopentane-2-imidazolin-5-one trifluoroacetate 180 mg of the product prepared in the previous step are treated with 3 ml of DCM and 4 ml of TFA for 45 minutes. After evaporation under vacuum, the residue is taken up in ether to give a white solid, which is filtered off, washed with ether and then dried under vacuum.

m=155 mg. M.p.=176°–178° C. NMR spectrum: 0.78 ppm: t: 3H: CH$_3$ (nBu) 1.25 ppm: sext: 2H: CH$_3$—C$\underline{H}_2$ 1.50 ppm: quint: 2H: CH$_3$—CH$_2$—C$\underline{H}_2$ 1.75–2.00: m: 8H: cyclopentane 2.65 ppm: t: 2$\underline{H}$: CH$_3$—CH$_2$—CH$_2$—C$\underline{H}_2$— 4.83 ppm: s: 2H: C$\underline{H}_2$—C$_6$H$_4$— 7.20–7.75 ppm: m: 8H: aromatic protons Mass spectrum: MH$^+$: 405

EXAMPLE 2

2-n-Butyl-1-[(2'-carboxybiphenyl-4-yl)methyl]-4-spirocyclopentane-2-imidazolin-5-one trifluoroacetate

Method 1

A) 2-n-Butyl-4-spirocyclopentane-2-imidazolin-5-one

The ethyl ester of 1-aminocyclopentanecarboxylic acid is prepared according to ADKINS and BILLICA (J. Amer. Chem. Soc., 1948, 70, 3121).

Ethyl valerimidate is prepared according to Mac ELVAIN (J. Amer. Chem. Soc., 1942, 64, 1825–1827) and then freed from its hydrochloride by reaction with potassium carbonate and extraction with DCM.

The ethyl ester of 1-aminocyclopentanecarboxylic acid (1.57 g) and ethyl valerimidate (1.56 g) are dissolved in 12 ml of xylene containing 6 drops of acetic acid. After refluxing for 6 and a half hours, the reaction medium is concentrated under vacuum and the residue is then chromatographed on silica gel using a chloroform/methanol/acetic acid mixture (94/4/2; v/v/v) as the eluent. The fraction containing the expected product is evaporated several times in the presence of xylene and then benzene in order to remove the acetic acid. 1.91 g of product are obtained in the form of a thick oil.

IR (CHCl$_3$): 1720 cm$^{-1}$: C=O 1635 cm$^{-1}$: C=N Note: The fact that there is no visible band between 1500 and 1600 cm$^{-1}$ indicates that, in chloroform solution, the product is an imidazolin-5-one. NMR spectrum: 0.92 ppm: t: 3H: CH$_3$ (nBu) 1.35 ppm: sext: 2H: CH$_3$—CH$_2$— 1.50-1.93 ppm: m: 10H: CH$_3$—CH$_2$—CH$_2$ and cyclopentane 2.33 ppm: t: 2H: CH$_3$—CH$_2$—CH$_2$—CH$_2$— 10.7 ppm: m: NH Mass spectrum: MH+: 195

The 2-n-butyl-4-spirocyclopentane-2-imidazolin-5-one prepared in step A can also be obtained by another procedure described below, using cyclopentanone as the starting material.

a) 1-Aminocyclopentanenitrile

This step is carried out according to A. Strecker (Org. Synth., 1955, 3).

1.97 g of sodium cyanide are dissolved in 3.9 ml of water in a round-bottomed flask and a solution containing 2.33 g of ammonium chloride in 5.9 ml of water and 3.5 ml of 20% aqueous ammonia is added; finally, 3 g of cyclopentanone in 3.8 ml of methanol are added to the flask. After stirring for 1 and a half hours, the mixture is heated at 60° C. for 45 minutes, heating is then stopped, stirring is continued for 45 minutes and the mixture is then cooled to 25° C. It is extracted several times with methylene chloride. The extracts are dried over sodium sulfate, filtered and concentrated under vacuum to give 4 g of the expected product in the form of an oil.

The 1-aminocyclopentanenitrile obtained is dissolved in 300 ml of acetone, and a solution of 2.25 g of oxalic acid dihydrate in 200 ml of acetone is added, with stirring. The precipitate formed is filtered off, washed with acetone and then dried.

m=4.71 g. M.p.=220° C.

This compound is 1-aminocyclopentanenitrile hemioxalate.

b) 1-Aminocyclopentaneacetamide

This step is carried out according to J. Zabicky (The Chemistry of Amides, Interscience, New York, 1970, 119).

5.1 g of the oxalate obtained in the previous step are treated with 7.65 ml of concentrated sulfuric acid (d=1.84) over 45 minutes, with stirring. The evolution of a gas is observed and the temperature rises to 100° C. The mixture is cooled to about 35° C. and poured into a mixture of ice and concentrated aqueous ammonia (10 g/2.8 ml). The suspension formed is extracted 6 times in succession with chloroform containing 5% of methanol. 3 ml of aqueous ammonia (d=0.92) are added to the aqueous phase and the mixture is extracted again with chloroform containing methanol (1/0.5; v/v). The combined organic phases are dried over sodium sulfate, filtered and concentrated. The expected product is obtained in the form of a white solid.

m=3.79 g. M.p.=95° C.

The structure can be confirmed by the results of analysis and the IR spectrum.

c) 2-n-Butyl-4-spirocyclopentane-2-imidazolin-5-one

This step is carried out according to H. Takenaka et al., Heterocycles, 1989, 29(6), 1185-89.

3 g of the compound prepared in the previous step are placed in 70 ml of anhydrous THF and 3.3 ml of triethylamine, and 3 ml of valeryl chloride in 10 ml of anhydrous THF are added, with stirring. A white suspension is formed. The intermediate which is formed, but not isolated, is 1-(N-valeryl)aminocyclopentanecarboxamide. 6 g of potassium hydroxide pellets, 7 ml of water and 16 ml of methanol are added. The mixture is refluxed for 2 and a half hours and 9 g of ammonium chloride are then added. After stirring for 15 minutes, the mixture is concentrated under vacuum. The residue obtained is taken up in 40 ml of water and extracted with 10 ml of ethyl acetate and then twice with 5 ml of ethyl acetate. The combined organic phases are dried over sodium sulfate and filtered. The filtrate is concentrated to dryness to give 4.85 g of the expected product. The NMR spectrum is similar to that described previously. The hydrochloride of this compound can be prepared by the addition of concentrated hydrochloric acid. The hydrochloride melts at 240° C. with sublimation.

B) 2-n-Butyl-4-spirocyclopentane-1-[(2'-tert-butoxycarbonylbiphenyl-4-yl)methyl]-2-imidazolin-5-one 970 mg of the product obtained in step A) are dissolved in 10 ml of DMF. 270 mg of sodium methylate are added and the mixture is stirred for 15 minutes at RT. 2.08 g of 4-bromomethyl-2'-tert-butoxycarbonylbiphenyl are added to the suspension and then, after 30 minutes, the mixture is heated at 40° C. for 3 and a half hours under nitrogen. The reaction medium is taken up in a mixture containing 100 ml of ethyl acetate, 10 ml of water and 1 ml of a saturated solution of sodium bicarbonate. The organic phase is washed with a saturated solution of sodium chloride and then dried over sodium sulfate and evaporated to dryness. The residue is chromatographed on silica gel using an ethyl acetate/toluene mixture (1/2; v/v) as the eluent to give 1.25 g of the expected product, which crystallizes.

M.p.=63°-66° C.

The IR and NMR spectra and the mass spectrum, as well as the Rf, are identical to those obtained in step D) of Example 1.

C) 2-n-Butyl-1-[(2'-carboxybiphenyl-4-yl)methyl]-4-spirocyclopentane-2-imidazolin-5-one trifluoroacetate 1.22 g of the product obtained in the previous step are stirred for 40 minutes in a solution containing 6 ml of DCM and 8 ml of TFA. After concentration under vacuum, the residue is taken up in ethyl ether; the white precipitate formed is filtered off, washed with ether and then dried under vacuum to give 1.15 g of the expected product.

M.p.=176°-178° C.

The IR and NMR spectra and the mass spectrum are identical to those obtained in Example 1E; likewise, the Rf observed in TLC is identical.

EXAMPLE 3

2-n-Butyl-1-[(2'-carboxybiphenyl-4-yl)methyl]-4-spirocyclopentane-2-imidazolin-5-one trifluoroacetate Method 3

A) 2-n-Butylbenzimidazole is prepared according to W. O. POOL (J. Amer. Chem. Soc., 1937, 59, 178) and 2-n-butyl-4,5,6,7-tetrahydrobenzimidazole is then prepared according to M. HARTMANN and L. PANIZZON (Helv. Chim. Acta, 1938, 21, 1692-1694).

M.p.=145° C. NMR spectrum: 0.82 ppm: t: 3H: CH$_3$ (nBu) 1.23 ppm: sext: 2H: CH$_3$—CH$_2$— 1.50 ppm: quint: 2H: CH$_3$—CH$_2$—CH$_2$— 1.65 ppm: s: 4H: H$_5$, H$_6$ (tetrahydrobenzimidazole) 2.35 ppm: s: 4H: H$_4$, H$_7$ (tetrahydrobenzimidazole) 2.45 ppm: t: 2H: CH$_3$—CH$_2$—CH$_2$—CH$_2$— 11.1 ppm: m: NH Mass spectrum: M+: 178

B) 2-n-Butyl-4-spirocyclopentane-1-[(2'-tert-butoxycarbonylbiphenyl-4-yl)methyl]-2-imidazolin-5-one 1 g of the product prepared in the previous step is dissolved in 45 ml of DMF with 303 mg of sodium methylate and a few mg of methylene blue. Oxygen is bubbled into the reaction medium, which is illuminated with a UV lamp. After 15 minutes, 2.14 g of 4- bromomethyl-2′-tert-butoxycarbonylbiphenyl are added and then, after 1 hour, the reaction medium is taken up in 300 ml of ethyl acetate to which 50 ml of water and 5 ml of a saturated solution of sodium bicarbonate have been added. The organic phase is then washed with a saturated solution of sodium chloride and subsequently dried over sodium sulfate and evaporated to dryness. The residue is chromatographed on silica gel using an ethyl acetate/toluene mixture (1/2; v/v) as the eluent to give 610 mg of the expected product, which crystallizes.

M.p.=62°-65° C.

The IR and NMR spectra and the mass spectrum, as well as the Rf, are identical to those obtained previously for the same compound.

C) 2-n-Butyl-1-[(2′-carboxybiphenyl-4-yl)methyl]-4-spirocyclopentane-2-imidazolin-5-one trifluoroacetate This compound is obtained by treatment in an acid medium as described in the last step of Example 1 and Example 2. The physicochemical data are identical to those obtained for the same compound prepared by method 1 or 2.

EXAMPLE 4

2-n-Butyl-4,4-dimethyl-1-[(2′-tert-butoxycarbonylbiphenyl-4-yl)methyl]-2-imidazolin-5-one and 2-n-butyl-1-[(2′-carboxybiphenyl-4-yl)methyl]-4,4-dimethyl-2-imidazolin-5-one trifluoroacetate Method 1

A) 2-n-Butyl-4,4-dimethyl-2-imidazolin-5-one

The ethyl ester of alpha-aminoisobutyric acid is prepared according to R. Jacquier et al. (Bull. Soc. Chim. France, 1971, (3), 1040–1051). 650 mg of this compound and 780 mg of ethyl valerimidate are dissolved in 8 ml of xylene containing 4 drops of acetic acid and the solution is refluxed for 7 hours. The reaction medium is then concentrated under vacuum and the residue is chromatographed on silica gel using a chloroform/methanol/acetic acid mixture (95/5/2; v/v/v) as the eluent. After several evaporations with xylene and then benzene to remove the acetic acid, 560 mg of the expected product are obtained, which crystallizes.

M.p.=35°-38° C. IR (CHCl$_3$): 1725 cm$^{-1}$: C=O 1635 cm$^{-1}$: C=N Note: The absence of a signal between 1500 and 1600 cm$^{-1}$ confirms that the compound present in chloroform solution is a 2-imidazolin-5-one. NMR spectrum: 0.92 ppm: t: 3H: CH$_3$ (nBu) 1.20 ppm: s: 6H: C(CH$_3$)$_2$ 1.38 ppm: sext: 2H: CH$_3$—CH$_2$ 1.63 ppm: quint: 2H: CH$_3$—CH$_2$—CH$_2$— 2.38 ppm: t: 2H: CH$_3$—CH$_2$—CH$_2$—CH$_2$— 10.7 ppm: m: 1H: N—H Mass spectrum: MH+: 169

B) 2-n-Butyl-4,4-dimethyl-1-[(2′-tert-butoxycarbonylbiphenyl-4-yl)methyl]-2-imidazolin-5-one 520 mg of the product prepared in the previous step are dissolved in 10 ml of DMF. 167 mg of sodium methylate are added and the mixture is stirred under nitrogen for 15 minutes. 1.25 g of 4-bromomethyl-2′-tert-butoxycarbonylbiphenyl are then added and the mixture is stirred at 40° C. for 3 and a half hours. The reaction medium is taken up in 150 ml of ethyl acetate and then 20 ml of water and 2 ml of a saturated solution of sodium bicarbonate. The organic phase is washed with a saturated solution of sodium chloride, dried over sodium sulfate and evaporated to dryness. The residue is chromatographed on silica gel using an ethyl acetate/toluene mixture (1.2/2; v/v) as the eluent to give 570 mg of the expected product, which crystallizes.

M.p.=98°-100° C. IR (CHCl$_3$): 1710-1720 cm$^{-1}$: C=O, C=O (imidazolinone, ester) 1625 cm$^{-1}$: C=N NMR spectrum: 0.78 ppm: t: 3H: CH$_3$ (nBu) 1.08 ppm: s: 9H: C(CH$_3$)$_3$ $$\left\{ \begin{array}{l} 1.15 \text{ ppm : s : C(CH}_3\text{)}_2 \\ 1.20 \text{ ppm : sext : CH}_3\text{—CH}_2\text{—} \end{array} \right\} 8H$$

1.45 ppm: quint: 2H: CH$_3$—CH$_2$—CH$_2$— 2.30 ppm: t: 2H: CH$_3$—CH$_2$—CH$_2$—CH$_2$— 4.65 ppm: s: 2H: CH$_2$—C$_6$H$_4$— 7.15-7.65 ppm: m: 8H: aromatic protons An NOE (Nuclear Overhauser Effect) study confirms the position of the 5-one and 4,4-dimethyl substituents on the imidazolinone. Mass spectrum: MH+: 435

C) 2-n-Butyl-1-[(2′-carboxybiphenyl-4-yl)methyl]-4,4-dimethyl-2-imidazolin-5-one trifluoroacetate 460 mg of the product prepared in the previous step are treated with 3 ml of DCM and 4 ml of TFA for 45 minutes. After concentration under vacuum, the residue is taken up in ether and the precipitate formed is filtered off, washed with ether and then dried under vacuum to give 450 mg of the expected product in the form of a white solid.

M.p.=168°-171° C. NMR spectrum: 0.82 ppm: t: 3H: CH$_3$ (nBu)

$$\left\{ \begin{array}{l} 1.30 \text{ ppm : sext : CH}_3\text{—CH}_2\text{—} \\ 1.35 \text{ ppm : s : C(CH}_3\text{)}_2\text{—} \end{array} \right\} 8H$$

1.55 ppm: quint: 2H: CH$_3$—CH$_2$—CH$_2$— 2.62 ppm: t: 2H: CH$_3$—CH$_2$—CH$_2$—CH$_2$— 4.82 ppm: s: 2H: CH$_2$—C$_6$H$_4$— 7.20-7.75; m: 8 aromatic H Mass spectrum: MH+: 379

EXAMPLE 5

1-[(2′-Cyanobiphenyl-4-yl)methyl]-2-n-butyl-4-spirocyclopentane-2-imidazolin-5-one and 2-n-butyl-4-spirocyclopentane-1-[(2′-(tetrazol-5-yl)biphenyl-4-yl)methyl]-2-imidazolin-5-one Method 1

A) 1-[(2′-Cyanobiphenyl-4-yl)methyl]-2-n-butyl-4-spirocyclopentane-2-imidazolin-5-one A mixture containing 250 mg of sodium hydride (as an 80% dispersion in mineral oil) and 5 ml of DMF is prepared under a nitrogen atmosphere and a solution containing 0.97 g of 2-n-butyl-4-spirocyclopentane-2-imidazolin-5-one (prepared in Example 2, step A) in 10 ml of DMF is added dropwise. The mixture is stirred for 30 minutes at RT and a solution of 1.5 g of 4-bromomethyl-2′-cyanobiphenyl in 10 ml of DMF is then added. After stirring for 1 hour at RT, the DMF is evaporated off under reduced pressure, the residue is then taken up with ethyl acetate and the organic phase is washed with water and then dried over sodium sulfate, filtered and evaporated. The residue is chromatographed on silica gel using a DCM/ethyl acetate mixture (9/1; v/v) as the eluent. 1.68 g of the expected product are recovered.

M.p.=92°-93° C.

B) 2-n-Butyl-4-spirocyclopentane-1-[(2′-(triphenylmethyltetrazol-5-yl)biphenyl-4-yl)methyl]-2-imidazolin-5-one 1.56 g of the previous product, 2.6 g of tributyltin azide and 30 ml of xylene are refluxed for 66 hours. The xylene is then evaporated off and the residue is dissolved in 20 ml of DCM and 5 ml of THF with the addition of 0.8 ml of 10N sodium hydroxide solution and, after stirring for 30 minutes, 2.5 g of trityl chloride, and the mixture is stirred for 26 hours. After evaporation of the solvents, the residue is taken up in ethyl acetate, washed with water and then with a 3% solution of potassium bisulfate and water. It is dried and evaporated. The residue is chromatographed on alumina using a hexane/ethyl acetate mixture (9/1; v/v) as the eluent to give 1.97 g of the expected product.

M.p.=150°–152° C.

C) 2-n-Butyl-4-spirocyclopentane-1-[(2'-(tetrazol-5-yl)biphenyl-4-yl)methyl]-2-imidazolin-5-one 1.96 g of the product prepared in the previous step are dissolved in 10 ml of methanol and 10 ml of THF. After the reaction medium has been cooled to 5° C., 1.5 ml of 4N hydrochloric acid are added and the mixture is stirred for 3 hours at RT and 1 hour at 30° C. After evaporation of the solvents, the residue is taken up in water and the pH is brought to 12 by the addition of 10N sodium hydroxide solution. The aqueous phase is extracted with ether, toluene and ether again. The aqueous phase is acidified to pH 2 by the addition of 1N hydrochloric acid and then extracted with ethyl acetate and the extract is dried and evaporated. The white solid obtained is dried at 50° C. under 0.05 mm of mercury to give 840 mg of the expected product.

M.p.=180°–181° C. NMR spectrum: 0.75 ppm: t: 3H: CH$_3$ (nBu) 1.10 ppm: sext: 2H: CH$_3$—CH$_2$— 1.20 ppm: quint: 2H: CH$_3$—CH$_2$—CH$_2$— 1.5–2 ppm: m: 8H: —C$_5$H$_8$ 2.2 ppm: t: 2H: CH$_3$—CH$_2$—CH$_2$—CH$_2$— 4.6 ppm: s: 2H: CH$_2$—C$_6$H$_4$— 7 ppm: s: 4H: CH$_2$—C$_6$H$_4$— 7.35–7.7 ppm: m: 4H: aromatic H$_{3',4',5',6'}$ An NOE study confirms the position of the 5-one substituent on the imidazole.

D) Potassium salt of 2-n-butyl-4-spirocyclopentane-1-[(2'-(tetrazol-5-yl)biphenyl-4-yl)methyl]-2-imidazolin-5-one 970 mg of the compound obtained in the previous step are dissolved in 40 ml of an isopropanol/methanol mixture (1/1; v/v) and the pH is adjusted to 12 by the addition of an 85% solution of potassium hydroxide in a methanol/water mixture (20/1; v/v). The reaction medium is evaporated, the residue is taken up in isopropanol and the medium is evaporated again. The residue is dissolved in 20 ml of isopropanol, with gentle heating, and then left to return to room temperature. The mixture is left to decant, the filtrate is evaporated and the residue is then taken up in heptane. After trituration, the product solidifies; it is filtered off and then washed again with heptane and dried under vacuum to give 945 mg of the expected potassium salt.

M.p.=142°–144° C. Elemental analysis: C$_{25}$H$_{27}$KN$_6$O.H$_2$O

| | | | | | | |
|---|---|---|---|---|---|---|
| calc. % | C: | 61.95 | H: | 6.03 | N: | 17.34 |
| found % | | 62.02 | | 6.13 | | 17.14 |

EXAMPLE 6

2-n-Butyl-1-[(2'-carboxybiphenyl-4-yl)methyl]-4-(4-spirotetrahydropyran)-2-imidazolin-5-one trifluoroacetate and
2-n-butyl-4-(4-spirotetrahydropyran)-1-[(2'-tert-butoxycarbonylbiphenyl-4-yl)methyl]-2-imidazolin-5-one Method 2

A) 4-Aminotetrahydropyran-4-carboxylic acid is prepared from tetrahydropyran-4-one by the method described in German patent 2 215 721.

B) 4-(N-Benzyloxycarbonylamino)-4-carboxytetrahydropyran 1.015 g of the compound of step A are placed in 12 ml of water and treated at 10° C. with 1.22 ml of diisopropylethylamine and then 3.33 g of N-(benzyloxycarbonyloxy)succinimide dissolved in 12 ml of acetonitrile. After 1 hour 15 minutes, the reaction medium is diluted with 70 ml of ethyl acetate and 10 ml of water and the pH is brought to 2 with a saturated solution of potassium bisulfate.

After decantation, the organic phase is washed with a saturated solution of sodium chloride, dried over sodium sulfate and then evaporated under vacuum. The residue is diluted with 60 ml of ether, after which 7 mmol of dicyclohexylamine are added. The precipitate formed is filtered off and washed with ether; it is then dissolved in an ethyl acetate/water mixture and the pH is brought to 1.5 with a saturated solution of potassium bisulfate. The organic phase is decanted, washed with a saturated solution of sodium chloride and evaporated under vacuum to give 1.9 g of a white solid.

M.p.=110°–115° C.

C) N-(2'-Tert-butoxycarbonylbiphenyl-4-ylmethyl)-4-(N-benzyloxycarbonylamino)tetrahydropyran-4-carboxamide 850 mg of the compound prepared in step B are dissolved in 15 ml of DMF, and equimolar amounts of 4-aminomethyl-2'-tert-butoxycarbonylbiphenyl, DIPEA and then BOP (10% excess) are added. After 40 minutes, the medium is taken up in 200 ml of ethyl acetate and 200 ml of water. The organic phase is decanted and then washed twice with a saturated solution of sodium bicarbonate, twice with a 5% solution of sodium bisulfate and then once with a saturated solution of sodium chloride. After drying over sodium sulfate, the organic phase is evaporated under vacuum to give 1.8 g of the expected product.

D) N-(2'-Tert-butoxycarbonylbiphenyl-4-ylmethyl)-4-aminotetrahydropyran-4-carboxamide The product obtained in step C is dissolved in 30 ml of methanol. 400 mg of 10% palladium-on-charcoal are added and the mixture is hydrogenated at atmospheric pressure. After 1 hour, the catalyst is filtered off and the filtrate is then concentrated under vacuum. The residue is chromatographed on silica using an ethyl acetate/methanol/33% aqueous ammonia mixture (99/1/0.5; v/v/v) as the eluent to give 0.93 g of the expected product in the form of a white solid.

M.p.=125°–127° C. NMR spectrum: 8.50 ppm: t: 1H: amide H 7.60–7.05 ppm: m: 8H: aromatic protons 4.25 ppm: d: 2H: CH$_2$—C$_6$H$_4$— 3.70–3.50 ppm: m: 4H: CH$_2$ in the 2 and 6 positions of the tetrahydropyran 2.00–1.80 ppm: m: 4H: CH$_2$ in the 3 and 5 positions of the tetrahydropyran 1.05 ppm: s: 9H: tBu E) 2-n-Butyl-4-(4-spirotetrahydropyran)-1-[(2'-tert-butoxycarbonylbiphenyl-4-yl)methyl]-2-imidazolin-5-one A mixture containing 0.9 g of the compound 2 obtained in step D, 327 mg of methyl orthovalerate and 5 drops of acetic acid is heated for 3 hours at 110° C. The reaction medium is taken up in 100 ml of ethyl acetate, then washed with a saturated solution of sodium bicarbonate and a saturated solution of sodium chloride and then dried over sodium sulfate and the ethyl acetate is evaporated off. The residue obtained is chromatographed on silica using an ethyl acetate/toluene mixture (2/1; v/v) as the eluent to give 550 mg of the expected product in the form of a wax.

NMR spectrum: 7.05–7.60 ppm: m: 8H: aromatic protons 4.63 ppm: s: 2H: C$\underline{H}_2$—C$_6$H$_4$— 3.85–3.55 ppm: m: 4H: C$\underline{H}_2$ in the 2 and 6 positions of the tetrahydropyran 2.30 ppm: t: 2H: C$\underline{H}_2$—C$_3$H$_7$ 1.05–1.80 ppm: m: 8H: C$\underline{H}_2$—C$\underline{H}_2$—C$\underline{H}_2$—C$\overline{H}_3$ and CH$_2$ in the 3 and 5 positions of the tetrahydropyran 1.03 ppm: s: 9H: tBu 0.75 ppm: t: 3H: (CH$_2$)$_3$—C$\underline{H}_3$ IR (CHCl$_3$): 1710–1720 cm$^{-1}$: C=O, C=O 1625 cm$^{-1}$: C=N F) 2-n-Butyl-4-(4-spirotetrahydropyran)-1-[(2'-tert-butoxycarbonylbiphenyl-4-yl)methyl]-2-imidazolin-5-one trifluoroacetate 530 mg of the product obtained in the previous step are treated with 4 ml of dichloromethane and 5 ml of TFA for 45 minutes. After evaporation under vacuum, the residue is taken up in ether and the precipitate formed is filtered off, washed with ether and then dried under vacuum to give 510 mg of the expected product.

M.p.=159°–162° C. NMR spectrum: 7.80–7.10 ppm: m: 8H: aromatic protons 4.80 ppm: s: 2H: C$\underline{H}_2$—C$_6$H$_4$— 4.00–3.75 ppm: m: 4H: C$\underline{H}_2$ in the 2 and 6 positions of the tetrahydropyran 2.60 ppm: t: 2H: C$\underline{H}_2$—C$_3$H$_7$ 1.45–2.00 ppm: m: 6H: C$\underline{H}_2$—C$\underline{H}_2$—C$\underline{H}_2$—C$\overline{H}_3$ and CH$_2$ in the 3 and 5 positions of the tetrahydropyran 1.30 ppm: sext: 2H: C$\underline{H}_2$—CH$_2$—CH$_2$—CH$_3$ 0.80 ppm: t: 3H: (CH$_2$)$_3$—C$\underline{H}_3$

EXAMPLE 7

2-n-Butyl-1-[(2'-carboxybiphenyl-4-yl)methyl]-4-[spiro(1-benzyl-4-piperidine)]-2-imidazolin-5-one trifluoroacetate and
2-n-butyl-4-[spiro(1-benzyl-4-piperidine)]-1-[(2'-tert-butoxycarbonylbiphenyl-4-yl)methyl]-2-imidazolin-5-one

Method 1

A) 4-Amino-1-benzylpiperidine-4-carboxylic acid is prepared from N-benzylpiperidin-4-one by the method described in German patent 2 215 721.

B) Ethyl 4-amino-1-benzylpiperidine-4-carboxylate 3.80 g of the compound prepared in step A are added to a solution of 13 g of hydrochloric acid in 50 ml of ethanol at 0° C. and the mixture is then refluxed for 5 hours. After concentration under vacuum, the residue is washed with ether and then dissolved in an ether/water mixture, to which a saturated solution of potassium carbonate is added to bring the pH to 9. The ether phase is decanted, washed with a saturated solution of sodium chloride, dried over sodium sulfate and then evaporated to dryness to give 3.50 g of the expected product in the form of an oil.

NMR spectrum: 7.20–7.40 ppm: m: 5H: aromatic protons 4.10 ppm: q: 2H: C$\underline{H}_2$—CH$_3$ 3.45 ppm: s: 2H: C$\underline{H}_2$ of the benzyl 2.25–2.60 ppm: m: 4H: C$\underline{H}_2$ in the 2

NMR spectrum:
7.20–7.40 ppm: m: 5 H: aromatic protons
4.10 ppm: q: 2 H: C$\underline{H}_2$—CH$_3$
3.45 ppm: s: 2 H: C$\underline{H}_2$ of the benzyl
2.25–2.60 ppm: m: 4 H: C$\underline{H}_2$ in the 2 and 6 positions of the piperidine
1.80–2.05 ppm: m: 2 H ⎫ C$\underline{H}_2$ in the 3 and 5 posi-
1.20–1.40 ppm: m: 2 H ⎭ tions of the piperidine
1.12 ppm: t: 3 H: C$\underline{H}_3$—CH$_2$—

1.12 ppm: t: 3H: C$\underline{H}_3$—CH$_2$—

C) 2-n-Butyl-4-[spiro(1-benzyl-4-piperidine)]-2-imidazolin-5-one

Ethyl valerimidate is prepared as in Example 2, step A. 2.06 g of ethyl valerimidate, 3.40 g of the compound prepared in step B and 8 drops of acetic acid are mixed in 15 ml of xylene and the mixture is refluxed for 6 hours. After concentration under vacuum, the residue is chromatographed on silica gel using a chloroform/methanol/acetic acid mixture (82/15/3; v/v/v) as the eluent. 2.80 g of the expected product are obtained after extraction with chloroform at pH 9 to remove the acetic acid.

M.p.=170°–172° C. IR (chloroform): 1725 cm$^{-1}$: C=O 1640 cm$^{-1}$: C=N NMR spectrum: 7.10–7.30 ppm: m: 5H: aromatic protons 3.45 ppm: s: 2H: —C$\underline{H}_2$—C$_6$H$_5$ 1.10–2.75 ppm: 5 m: 14H: C$\underline{H}_2$ in the 2, 3, 5 and 6 positions of the piperidine and (CH$_2$)$_3$—C$\underline{H}_3$ 0.80 ppm: t: 3H: (CH$_2$)$_3$—C$\underline{H}_3$ D) 2-n-Butyl-4-[spiro(1-benzyl-4-piperidine)]-1-[(2'-tert-butoxycarbonylbiphenyl-4-yl)methyl]-2-imidazolin-5-one 513 mg of sodium methylate and, after 15 minutes, 4.16 g of 4-bromomethyl-2'-tert-butoxycarbonylbiphenyl are added to a solution of 2.78 g of the compound obtained in step C in 25 ml of DMF. The reaction medium is heated at 40° C. for 5 hours and then taken up in 300 ml of ethyl acetate, 50 ml of water and 5 ml of a saturated solution of sodium bicarbonate. The organic phase is decanted, washed once more with a saturated solution of sodium chloride, dried over sodium sulfate and evaporated under vacuum. The residue is chromatographed on silica using an ethyl acetate/methanol mixture (95/5; v/v) as the eluent to give 0.98 g of the expected product.

M.p.=103°–106° C. IR (CHCl$_3$): 1710–1725 cm$^{-1}$: C=O, C=O (imidazoline, ester) 1630 cm$^{-1}$: C=N NMR spectrum: 7.70–7.10 ppm: m: 13H: aromatic protons 4.70 ppm: s: 2H: C$\underline{H}_2$—C$_6$H$_4$— 3.55 ppm: s: 2H: C$\underline{H}_2$—C$_6$H$_5$ 1.20–2.75 ppm: 5 m: 14H: C$\underline{H}_2$ in the 2, 3, 5 and 6 positions of the piperidine and (CH$_2$)$_3$—C$\underline{H}_3$ 1.15 ppm: s: 9H: tBu 0.85 ppm: t: 3H: (CH$_2$)$_3$—C$\underline{H}_3$ E) 2-n-Butyl-1-[(2'-carboxybiphenyl-4-yl)methyl]-4-[spiro(1-benzyl-4-piperidine)]-2-imidazolin-5-one trifluoroacetate 350 mg of the compound obtained in step D are dissolved in 4 ml of dichloromethane and 5 ml of TFA. After 45 minutes, the medium is concentrated under vacuum, the residue is then taken up in an ether/hexane mixture and the precipitate formed is filtered off, washed with ether and dried under vacuum to give 350 mg of the expected product.

M.p.=198°–200° C. NMR spectrum: 7.05–7.75 ppm: m: 13H: aromatic protons 4.75 ppm: s: 2H: C$\underline{H}_2$—C$_6$H$_4$— 4.40 ppm: s: 2H: C$\underline{H}_2$—C$_6$H$_5$ 3.20–3.60 ppm: m: 4H: C$\underline{H}_2$ in the 2 and 6 positions of the piperidine 2.35 ppm: t: 2H: C$\underline{H}_2$—CH$_2$—CH$_2$—CH$_3$ 2.20–1.40 ppm: 3 unresolved signals: CH$_2$ in the 3 and 5 positions of the piperidine and CH$_2$—C$\underline{H}_2$—CH$_2$—CH$_3$ 1.25 ppm: sext: 2H: CH$_2$—CH$_2$—C$\underline{H}_2$—CH$_3$ 0.80 ppm: t: 3H: (CH$_2$)$_3$—C$\underline{H}_3$

EXAMPLE 8

2-n-Butyl-1-[(2'-carboxybiphenyl-4-yl)methyl]-4-(4-spiropiperidine)-2-imidazolin-5-one ditrifluoroacetate
and
2-butyl-4-(4-spiropiperidine)-1-[(2'-tert-butoxycarbonylbiphenyl-4-yl)methyl]-2-imidazolin-5-one A) 2-n-Butyl-4-(4-spiropiperidine)-1-[(2'-tert-butoxycarbonylbiphenyl-4-yl)methyl]-2-imidazolin-5-one 300 mg of the compound of Example 7, step D, are dissolved in 10 ml of methanol. 180 mg of 10% palladium-on-charcoal are added and the mixture is hydrogenated for 3 hours at atmospheric pressure. The catalyst is filtered off and the filtrate is concentrated under vacuum to give 200 mg of the expected product.

NMR spectrum: 7.20–7.75 ppm: m: 8H: aromatic protons 4.75 ppm: s: 2H: C$\underline{H}_2$—C$_6$H$_4$— 3.00–1.70 ppm: 3 unresolved signals for the 4 CH$_2$ of the piperidine 2.40 ppm: t: 2H: C$\underline{H}_2$—CH$_2$—CH$_2$—CH$_3$ 1.60 ppm: quint: 2H: CH$_2$—C$\underline{H}_2$—CH$_2$—CH$_3$ 1.35 ppm: sext: 2H: CH$_2$—CH$_2$—C$\underline{H}_2$—CH$_3$ 1.20 ppm: s: 9H: tBu 0.90 ppm: t: 3H: (CH$_2$)$_3$—C$\underline{H}_3$ B) 2-n-Butyl-1-[(2'-carboxybiphenyl-4-yl)methyl]4-(4-spiropiperidine)-2-imidazolin-5-one ditrifluoroacetate 160 mg of the product obtained in step A are stirred for 45 minutes in 3 ml of dichloromethane and 4 ml of trifluoroacetic acid. The mixture is concentrated under vacuum and the residue is taken up in ether to give a gum and then a foam after drying under vacuum (150 mg).

M.p.=80°–85° C. NMR spectrum: 7.15–7.80 ppm: m: 8H: aromatic protons 4.75 ppm: s: 2H: C$\underline{H}_2$—C$_6$H$_4$— 3.20–1.60 ppm: 3 unresolved signals: 4 CH$_2$ of the piperidine 2.40 ppm: t: 2H: C$\underline{H}_2$—CH$_2$—CH$_2$—CH$_3$ 1.50 ppm: quint: 2H: CH$_2$—C$\underline{H}_2$—CH$_2$—CH$_3$ 1.30 ppm: sext: 2H: CH$_2$—CH$_2$—C$\underline{H}_2$—CH$_3$ 0.80 ppm: t: 3H: (CH$_2$)$_3$—C$\underline{H}_3$

EXAMPLE 9

2-n-Butyl-1-[(2'-carboxybiphenyl-4-yl)methyl]-4,4-diphenyl-2-imidazolin-5-one trifluoroacetate and
2-n-butyl-4,4-diphenyl-1-[(2'-tert-butoxycarbonylbiphenyl-4-yl)methyl]-2-imidazolin-5-one

Method 1

A) Valeramidine hydrochloride 6 g of ethyl valerimidate hydrochloride are added to a solution of 6.75 g of ammonia in 80 ml of methanol at 0° C. After 18 h, the reaction medium is concentrated under vacuum to give the expected product in the form of a white solid.

B) 2-n-Butyl-4,4-diphenyl-2-imidazolin-5-one

This compound is prepared according to the procedure described by J. NYITRAI and K. LEMPERT in Tetrahedron, 1969, 25, 4265–4275, from benzil and valeramidine hydrochloride.

M.p.=135° C. IR (CHCl$_3$): 1725 cm$^{-1}$: C=O 1640 cm$^{-1}$: C=N NMR spectrum: 7.20–7.50 ppm: m: 10H: aromatic protons 2.50 ppm: t: 2H: C$\underline{H}_2$—CH$_2$—CH$_3$ 1.65 ppm: quint: 2H: CH$_2$—C$\underline{H}_2$—CH$_2$—CH$_2$CH$_3$ 1.35 ppm: sext: 2H: CH$_2$—CH$_2$—C$\underline{H}_2$—CH$_3$ 0.90 ppm: t: 3H: CH$_2$—CH$_2$—CH$_2$—C$\underline{H}_3$ 11 ppm: sb: NH C) 2-n-Butyl-4,4-diphenyl-1-[(2'-tert-butoxycarbonylbiphenyl-4-yl)methyl]-2-imidazolin-5-one This compound is prepared according to the usual method by reacting 4-bromomethyl-2'-tert-butoxycarbonylbiphenyl with the compound prepared in step B, in the presence of sodium methylate in DMF.

IR (CHCl$_3$): 1715–1725 cm$^{-1}$: C=O, C=O (ester, imidazolinone) 1635 cm$^{-1}$: C=N NMR spectrum: 7.25–7.80 ppm: m: 18H: aromatic protons 4.85 ppm: s: 2H: N—C$\underline{H}_2$—C$_6$H$_4$— 2.60 ppm: t: 2H: C$\underline{H}_2$—CH$_2$—CH$_2$—CH$_3$ 1.75 ppm: quint: 2H: CH$_2$—C$\underline{H}_2$—CH$_2$—CH$_3$ 1.40 ppm: sext: 2H: CH$_2$—CH$_2$—C$\underline{H}_2$—CH$_3$ 1.15 ppm: s: 9H: tBu 0.90 ppm: t: 3H: CH$_3$ of the n-butyl D) 2-n-Butyl-1-[(2'-carboxybiphenyl-4-yl)methyl]-4,4-diphenyl-2-imidazolin-5-one trifluoroacetate 500 mg of the product prepared in step C are treated with 2.5 ml of dichloromethane and 2.5 ml of trifluoroacetic acid at 20° C. for 40 minutes. After concentration under vacuum, the residue is taken up in an ether/hexane mixture and the precipitate formed is filtered off, washed with hexane and dried to give 440 mg of the expected product.

M.p.=55°–60° C. NMR spectrum: 7.15–7.80 ppm: m: 18H: aromatic protons 4.85 ppm: s: 2H: N—C$\underline{H}_2$—C$_6$H$_4$— 2.60 ppm: t: 2H: C$\underline{H}_2$—CH$_2$—CH$_2$—C$\underline{H}_3$ 1.70 ppm: quint: 2H: CH$_2$—C$\underline{H}_2$—CH$_2$—CH$_3$ 1.40 ppm: sext: 2H: CH$_2$—CH$_2$—C$\underline{H}_2$—CH$_3$ 0.90 ppm: t: 3H: CH$_3$ of the butyl

EXAMPLE 10

2-n-Butyl-3-[(2'-carboxybiphenyl-4-yl)methyl]-6-spirocyclopentane-5,6-dihydro-1H-pyrimidin-4-one trifluoroacetate A) (1-Aminocyclopentyl)acetic acid Cyclopentylideneacetic acid is prepared according to G. A. R. KON and R. P. LINSTEAD, J. Chem. Soc., 1925, 127, 616. 740 mg of this acid and 5 ml of 20% aqueous ammonia are placed in an autoclave and the mixture is heated at 150° C. for 24 hours. After evaporation of the solvents, the residue is chromatographed on a silica column using a DCM/methanol/20% aqueous ammonia solution mixture (70/30/1; v/v/v) as the eluent to give 330 mg of the expected acid.

B) Ethyl (1-aminocyclopentyl)acetate 330 mg of the acid are dissolved in 10 ml of ethanol. The solution is cooled in an ice bath and saturated with gaseous hydrochloric acid. After 24 hours under reflux, the reaction medium is evaporated, the residue is taken up in a solution of sodium carbonate and extracted with ethyl acetate and the extract is then dried over sodium sulfate, filtered and evaporated to give 312 mg of the expected ester.

C) 2-n-Butyl-6-spirocyclopentane-5,6-dihydro-1H-pyrimidin-4-one

A mixture containing 310 mg of the compound obtained in step B, 348 mg of ethyl valerimidate, 10 ml of xylene and 6 drops of acetic acid is brought to the reflux point. After 2 hours and 18 hours, a further 348 mg of ethyl valerimidate are added and, after a total reflux time of 24 hours, the reaction medium is evaporated and then chromatographed on silica using a DCM/methanol mixture (97/3; v/v) as the eluent to give 153 mg of the expected product.

D) 2-n-Butyl-6-spirocyclopentane-3-[(2'-tert-butoxycarbonylbiphenyl-4-yl)methyl]-4(1H)5,6-dihydropyrimidin-4-one A mixture of 10 ml of DMF and 40 mg of sodium hydride as an 80% dispersion in oil is prepared under a nitrogen atmosphere. 144 mg of the compound prepared in step C, dissolved in 5 ml of DMF, are added dropwise at room temperature. After stirring for 30 minutes, a solution of 288 mg of 4-bromomethyl-2'-tert-butoxycarbonylbiphenyl in 5 ml of DMF is added. The mixture is stirred for 2 hours and then evaporated and the residue is taken up in water and extracted with ethyl acetate. The extract is dried over sodium sulfate, filtered, evaporated and then purified by column chromatography using a hexane/ethyl acetate mixture (85/5; v/v) as the eluent to give 174 mg of the expected product.

E)

10 ml of trifluoroacetic acid are cooled in a bath of iced water and 161 mg of the compound prepared in step D are added. The mixture is stirred for 30 minutes and then evaporated. The residue is taken up in ethyl ether and the mixture is then evaporated again. This operation is repeated and the residue is then dried under vacuum to give 140 mg of the expected compound in the form of an amorphous powder.

M.p.=108°–115° C. NMR spectrum: 0.9 ppm: t: 3H: $(CH_2)_3$—$CH_3$ 1.1 to 2.1 ppm: m: 12H: cyclopentane and $CH_2$—$CH_2$—$CH_2$—$CH_3$ 2.7 ppm: t: 2H: $CH_2$—$CH_2$—$CH_2$—$CH_3$ 3.1 ppm: s: 2H: —$CH_2$—CO 5.1 ppm: s: 2H: N—$CH_2$—$C_6C_5$ 7.2 to 7.8 ppm: m: 8H: aromatic protons

EXAMPLE 11

2-n-Butyl-4-spirocyclopentane-1-[(2'-tert-butoxycarbonylbiphenyl-4-yl)methyl]-2-imidazolin-5-thione and 2-n-butyl-1-[(2'-carboxybiphenyl-4-yl)methyl]-4-spirocyclopentane-2-imidazolin-5-thione trifluoroacetate A) 2-n-Butyl-4-spirocyclopentane-1-[(2'-tert-butoxycarbonylbiphenyl-4-yl)methyl]-2-imidazolin-5-thione 5.63 g of the compound prepared in Example 1, step D, are dissolved in 40 ml of anhydrous toluene and treated with 3 g of Lawesson's reagent at 80° C. under nitrogen. After 6 hours, the reaction mixture is filtered and concentrated. The concentrate is chromatographed on silica using a DCM/ethyl acetate mixture (95/5; v/v) as the eluent to give the expected product in the form of an oil, which crystallizes in the cold.

m=4.5 g. M.p.=77°–79° C. NMR spectrum: 0.90 ppm: t: 3H: $CH_3$ (nBu) 1.20 ppm: s: 9H: tBu 1.35 ppm: sext: 2H: $CH_3$—$CH_2$— 1.60 ppm: quint: 2H: $CH_3$—$CH_2$—$CH_2$— 1.80-2.10 ppm: m: 8H: cyclopentane 2.60 ppm: t: 2H: $CH_3$—$CH_2$—$CH_2CH_2$ 5.35 ppm: s: 2H: $CH_2$—$C_6H_4$— 7.25-7.80 ppm: m: 8H: aromatic protons B) 2-n-Butyl-1-[(2'-carboxybiphenyl-4-yl)methyl]-4-spirocyclopentane-2-imidazolin-5-thione trifluoroacetate 225 mg of the compound obtained in step A are treated with 5 ml of DCM and 5 ml of TFA for 30 minutes. After concentration, the residue is taken up in ether. The expected compound is obtained in the form of a yellow powder, which is filtered off and then rinsed with hexane.

m=160 mg. M.p.=185°–190° C. Mass spectrum: MH+: 421 NMR spectrum: 0.78 ppm: t: 3H: $CH_3$ (nBu) 1.20 ppm: sext: 2H: $CH_3$—$CH_2$ 1.50 ppm: quint: 2H: $CH_3$—$CH_2$—$CH_2$— 1.75-2.00 ppm: m: 8H: cyclopentane 2.40 ppm: t: 2H: $CH_3$—$CH_2$—$CH_2$—$CH_2$ 5.20 ppm: s: 2H: $CH_2$—$C_6H_4$— 7.00-7.65 ppm: m: 8H: aromatic protons

EXAMPLE 12

2-n-Butyl-4-(2-spiroindane)-1-[(2'-tert-butoxycarbonylbiphenyl-4-yl)methyl]-2-imidazolin-5-one and 2-n-butyl-1-[(2'-carboxybiphenyl-4-yl)methyl]4-(2-spiroindane)-2-imidazolin-5-one

Method 1

A) 2-Aminoindane-2-carboxylic acid is prepared according to R. M. Pinder, J. Med. Chem., 1971, 14, 9, 892, and the corresponding ethyl ester is then prepared according to Adkins (ref. cited in Example 2A).

B) 2-n-Butyl-4-(2-spiroindane)-2-imidazolin-5-one 2.78 g of the ethyl ester prepared in step A and 2.5 g of ethyl valerimidate are dissolved in 20 ml of xylene in the presence of 60 μl of acetic acid and refluxed for 3 hours. A further 500 mg of ethyl valerimidate are added and reflux is maintained for a further 3 hours. The reaction medium is concentrated and then chromatographed on silica using a hexane/ethyl acetate/acetic acid mixture (3/8/0.3; v/v/v) as the eluent. The pure fractions are combined and evaporated with toluene to give 3.07 g of the expected product in the form of a white solid.

M.p.=148°–150° C. NMR spectrum: 0.90 ppm: t: 3H: $CH_3$ (nBu) 1.2-1.7 ppm: m: 4H: $CH_2$—$CH_2$—$CH_3$ 2.4 ppm: t: 2H: $CH_2$—$(CH_2)_2$—$CH_3$ 2.8-3.2 ppm: q: 4H: $2CH_2$ (indane) 4.90 ppm: s: 2H: $CH_2$—$C_6H_4$— 7.2 ppm: m: 4H: aromatic protons C) 2-n-Butyl-4-(2-spiroindane)-1-[(2'-tert-butoxycarbonylbiphenyl-4-yl)methyl]-2-imidazolin-5-one The compound obtained in the previous step is dissolved in 20 ml of anhydrous DMF and treated with 450 mg of sodium methylate under nitrogen. After 20 minutes at room temperature, 3.6 g of 4-bromomethyl-2'-tert-butoxycarbonylbiphenyl are added and the mixture is stirred at 40° C. for 6 hours. The reaction medium is concentrated, the usual washes are then carried out and the product is chromatographed on silica using dichloromethane/ethyl acetate (95/5; v/v) as the eluent to give the expected compound in the form of a foam (m=1.84 g).

NMR spectrum: 0.80 ppm: t: 3H: $CH_3$ (nBu) 1.20 ppm: s: 9H: tBu 1.20-1.60 ppm: m: 4H: $CH_2$—$CH_2$—$CH_3$ 2.40 ppm: t: 2H: $CH_2$—$(CH_2)_2$—$CH_3$ 2.9-3.3 ppm: q: 4H: $2CH_2$ (indane) 4.80 ppm: s: 2H: N—$CH_2$—$C_6H_4$— 7.20-7.80 ppm: m: 12H: aromatic protons D) 2-n-Butyl-1-[(2'-carboxybiphenyl-4-yl)methyl]-4-(2-spiroindane)-2-imidazolin-5-one 1.71 g of the compound obtained in the previous step are dissolved in 15 ml of DCM and treated with 20 ml of TFA. After 30 minutes, the reaction medium is concentrated and then taken up in ether. After trituration, the solid obtained is filtered off, rinsed with ether and dried to give 1.42 g of the expected product.

M.p.=217°–218° C. NMR spectrum: 0.70 ppm: t: 3H: $CH_3$ (nBu) 1.10-1.50 ppm: m: 4H: $CH_2$—$CH_2$—$CH_3$ 2.30 ppm: t: 2H: $CH_2$—$(CH_2)_2$—$CH_3$ 2.8-3.3 ppm: q: 4H: $2CH_2$ (indane) 4.70 ppm: s: 2H: N—$CH_2$—$C_6H_4$— 7.1-7.7 ppm: m: 12H: aromatic protons Other compounds according to the invention were prepared by one of the methods described above. They are collated in Table 1. The structure of each of these compounds is consistent with the analysis of their NMR spectra.

EXAMPLE 13

2-n-Butyl-1-[(2'-(imidazol-1-ylcarbonyl)biphenyl-4-yl)methyl]-4-spirocyclopentane-2-imidazolin-5-one

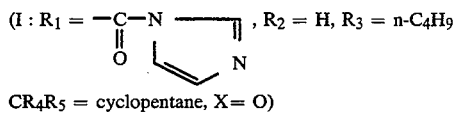

(I : R₁ = —C—N⇌N, R₂ = H, R₃ = n-C₄H₉

$CR_4R_5$ = cyclopentane, X= O)

A mixture containing 404 mg of the compound prepared in Example 1, step E, 15 ml of THF and 260 mg of carbonyldiimidazole is stirred at room temperature for 72 hours. The reaction medium is evaporated, the residue is taken up in ethyl acetate and the mixture is washed with water and then with a solution of sodium chloride to give 420 mg of product, which are purified by chromatography on silica using a DCM/ethyl acetate mixture (70/30; v/v) as the eluent to give the expected compound.

m=230 mg. M.p.=120° C.

EXAMPLE 14

2-n-Butyl-1-[(2'-(3-cyano-2-methylisothioureidomethyl)biphenyl-4-yl)methyl]-4-spirocyclopentane-2-imidazolin-5-one

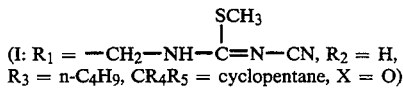

(I: R₁ = —CH₂—NH—C=N—CN, R₂ = H, R₃ = n-C₄H₉, $CR_4R_5$ = cyclopentane, X = O)

A) 1-[(2'-Aminomethylbiphenyl-4-yl)methyl]-2-n-butyl-4-spirocyclopentane-2-imidazolin-5-one This compound is obtained by hydrogenation of the compound prepared in Example 5.

1 g of the compound prepared in Example 5, step A, is placed in 15 ml of absolute methanol and 2.3 ml of ethanol in the presence of 0.5 g of 5% palladium-on-charcoal and the mixture is hydrogenated at room temperature for 24 hours. After treatment, 730 mg of the expected product are obtained in the form of an oil.

B)

A mixture containing 300 mg of the compound prepared in the previous step and 113 mg of N-cyanimido-S,S-dimethyldithiocarbonate in 3 ml of ethanol is refluxed for 24 hours. After the usual treatment, the reaction medium is purified by chromatography on silica using a DCM/ethyl acetate mixture (50/50; v/v) as the eluent. The expected product is isolated in the form of a white solid.

m=307 mg. M.p.=83° C.

EXAMPLE 15

2-n-Butyl-1-[(2'-(2-cyanoguanidinomethyl)biphenyl-4-yl)methyl]-4-spirocyclopentane-2-imidazolin-5-one

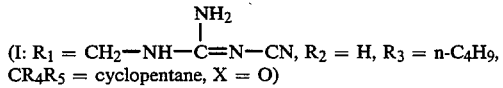

(I: R₁ = CH₂—NH—C=N—CN, R₂ = H, R₃ = n-C₄H₉, $CR_4R_5$ = cyclopentane, X = O)

This compound is obtained from the compound prepared in the previous Example. 200 mg of the compound are placed in 10 ml of absolute ethanol and the mixture is saturated with ammonia at about 10° C. and then heated at 80° C. in an autoclave overnight. After concentration of the reaction medium to dryness, the residue is chromatographed on silica using a DCM/methanol mixture (95/5; v/v) as the eluent to give 130 mg of the expected product.

M.p.=100° C.

EXAMPLE 16

2-n-Butyl-4-spirocyclopentane-1-[(2'-trifluoromethylsulfonylaminobiphenyl-4-yl)methyl]-2-imidazolin-5-one trifluoromethylsulfonate

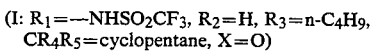

(I: R₁=—NHSO₂CF₃, R₂=H, R₃=n-C₄H₉, $CR_4R_5$=cyclopentane, X=O)

A) 4-Methyl-2'-nitrobiphenyl 11.2 g of 2-nitrobromobenzene are mixed with 15 g of 4-iodotoluene and the mixture is heated to 195° C. and stirred at this temperature for 3 and a half hours. After returning to room temperature, it is taken up in DCM and heated to the reflux point, the hot solution is filtered on Celite ® and the DCM is then evaporated off.

m=6.5 g. B.p.=80°-120° C. under 0.2 mm Hg, $n_D^{24}$=1.6042.

B) 4-Bromomethyl-2'-nitrobiphenyl

A mixture containing 6.5 g of 4-methyl-2'-nitrobiphenyl, 5.42 g of NBS, 118 mg of azo-bis-isobutyronitrile and 500 ml of carbon tetrachloride is refluxed for 5 hours. It is cooled to 0° C. and filtered and the filtrate is concentrated to give 9 g of an oily product, which is used as such in the next step.

C) 2-n-Butyl-1-[(2'-nitrobiphenyl-4-yl)methyl]-4-spirocyclopentane-2-imidazolin-5-one A mixture containing 260 mg of 80% sodium hydride in 5 ml of DMF is prepared and 500 mg of 2-n-butyl-4-spirocyclopentane-2-imidazolin-5-one, prepared in Example 2, step A, are added at room temperature under nitrogen. After stirring for 15 minutes, 901 mg of 4-bromomethyl-2'-nitrobiphenyl in 5 ml of DMF are added and stirring is continued for 24 hours. The reaction medium is concentrated to dryness and the residue is taken up in a water/ethyl acetate mixture. The organic phase is decanted, dried over sodium sulfate and filtered and the ethyl acetate is then evaporated off. The product obtained is chromatographed on silica using a DCM/ethyl acetate mixture (9/1; v/v) as the eluent to give 500 mg of the expected product.

D) 1-[(2'-Aminobiphenyl-4-yl)methyl]-2-n-butyl-4-spirocyclopentane-2-imidazolin-5-one 450 mg of the product obtained in the previous step are placed in 10 ml of methanol in the presence of 5% palladium-on-charcoal, at room temperature, for hydrogenation. After filtration of the catalyst and evaporation, 240 mg of the expected product are obtained.

E)

In 4 ml of DCM, 225 mg of the product obtained in the previous step are mixed with 0.1 ml of triethylamine, 0.2 ml of trifluoromethylsulfonic anhydride is added under argon at −78° C. and the mixture is then left to return to room temperature. The reaction medium is washed with water and a solution of sodium bicarbonate and then dried and concentrated to give 150 mg of an amorphous white solid.

NMR spectrum: 0.4–1.3 ppm: m: 7H: CH₃—CH₂—CH₂— 1.4–2.3 ppm: m: 10H: CH₃—CH₂—CH₂—CH₂ and cyclopentane 4–4.8 ppm: AB system: 2H: N—CH₂—C₆H₄— 7–7.6 ppm: m: 8H: aromatic protons 8.3 ppm: s: 1H: —NH 10 ppm: sb: 1H: CF₃SO₃H

EXAMPLE 17

2-n-Butyl-4-spirocyclopentane-1-[(2'-trifluoromethyl-sulfonylaminomethylbiphenyl-4-yl)methyl]-2-imidazolin-5-one trifluoromethylsulfonate (I: $R_1=CH_2NHSO_2CF_3$, $R_2=H$, $R_3=n\text{-}C_4H_9$, $CR_4R_5=$cyclopentane, $X=O$)

The preparation is effected starting from the 1-[(2'-aminomethylbiphenyl-4-yl)methyl]-2-n-butyl-4-spirocyclopentane-2-imidazolin-5-one prepared in Example 14, step A. 322 mg of this compound and 0.122 ml of triethylamine are placed in 3.4 ml of DCM at $-70°$ C. and 0.294 ml of trifluoromethylsulfonic anhydride is added. The mixture is left to return to room temperature, poured into dilute acetic acid and extracted with DCM, the extract is dried over sodium sulfate and filtered and the DCM is evaporated off. The residue is chromatographed twice on silica using DCM/ethyl acetate (95/5; v/v, then 99.5/0.5; v/v) as the eluent.

This gives m=90 mg. M.p.=90° C. NMR spectrum: 0.4–1.2 ppm: m: 7H: —$CH_2$—$CH_2$—$CH_3$ 1.3–2.45 ppm: m: 10H: $CH_2$—$CH_2$—$CH_2$—$CH_3$ and cyclopentane 4.1–5 ppm: m: 4H: N—$CH_2$—$C_6H_4$— and NH —$CH_2$—$C_6H_4$— 7.1–7.7 ppm: m: 8H: aromatic protons 8.4 ppm: s: 1H: NH

EXAMPLE 18

2-n-Butyl-1-[(2'-(N-hydroxycarbamoyl)biphenyl-4-yl)methyl]-4-spirocyclopentane-2-imidazolin-5-one (I: $R_1=$—CO—NHOH, $R_2=H$, $R_3=n\text{-}C_4H_9$, $CR_4R_5=$cyclopentane, $X=O$)

The compound prepared in Example 2 is freed from its trifluoroacetic acid salt by taking up this compound in an ethyl acetate/water mixture and bringing the solution to pH 6 by the addition of a saturated solution of sodium bicarbonate. The organic phase is washed with a saturated solution of sodium chloride, dried over sodium sulfate, filtered and concentrated to give the free base in the form of a white solid.

450 mg of this compound are dissolved in chloroform, 860 ml of thionyl chloride are added at 0° C. and the mixture is stirred at room temperature for 2 hours. The solution is concentrated and the traces of thionyl chloride are removed by azeotropic distillation with toluene. The acid chloride thus obtained is added dropwise in DMF solution to a solution containing 200 mg of hydroxylamine hydrochloride and 700 µl of DIPEA in 10 ml of DMF. After 2 hours at 0° C., the reaction medium is concentrated and the concentrate is taken up in 100 ml of DCM and 50 ml of water. The mixture is brought to pH 7 and the organic phase is extracted and then dried over sodium sulfate. After filtration, the solution is concentrated. The product obtained is recrystallized from an ethyl acetate/ethyl ether/hexane mixture.

m=360 mg. M.p.=85° C.

EXAMPLE 19

2-n-Butyl-4-spirocyclopentane-1-[(2'-ureidobiphenyl-4-yl)methyl]-2-imidazolin-5-one (I: $R_1=NHCONH_2$, $R_2=H$, $R_3=n\text{-}C_4H_9$, $CR_4R_5=$cyclopentane, $X=O$)

This compound is prepared using the method described by B. B. Kobu et al. in Org. Synth., 1957, 37, 52, starting from the 1-[(2'-aminobiphenyl-4-yl)methyl]-2-n-butyl-4-spirocyclopentane-2-imidazolin-5-one prepared in Example 14, step A.

1 g of the latter is dissolved in 50 ml of 6N hydrochloric acid and treated with potassium isocyanate for 1 hour at 5° C. The reaction medium is concentrated, the concentrate is taken up in ethyl acetate and the mixture is washed with sodium bicarbonate and then with a saturated solution of sodium chloride. After drying over sodium sulfate and filtration, the solution is concentrated and the oil obtained is purified by chromatography on silica using a DCM/methanol mixture (9/1; v/v) as the eluent.

m=600 mg. NMR spectrum: 0.85 ppm: t: 3H: $CH_2$—$CH_3$ 1.35 ppm: sext: 2H: $CH_2$—$CH_3$ 1.6 ppm: quint: 2H: $CH_2$—$CH_2$—$CH_3$ 1.7–2 ppm: m: 8H: cyclopentane 2.45 ppm: t: 2H: $CH_2$—$CH_2$—$CH_2$—$CH_3$ 4.8 ppm: s: 2H: —$CH_2$—$C_6H_4$— 6.05 ppm: s: 2H: $NH_2$ 7–8 ppm: m: 9H: 8 aromatic H+NHCO

EXAMPLES 20 AND 21

1-[(2'-Carboxybiphenyl-4-yl)methyl]-2-n-propyl-4-spirocyclohexane-2-imidazolin-5-one and
1-[(2'-N-cyanocarboxamidebiphenyl-4-yl)methyl]-2-n-propyl-4-spirocyclohexane-2-imidazolin-5-one (I: $R_1=CO$—NH—CN, $R_2=H$, $R_3=n\text{-}C_3H_7$, $CR_4R_5=$cyclohexane, $X=O$)

A) Ethyl butyrimidate hydrochloride

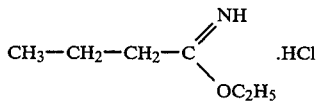

This compound is prepared according to Mc Elvain (J. Amer. Chem. Soc., 1942, 64, 1825–1827).

23 ml of butyronitrile are added at 0° C. to a solution of 10.6 g of gaseous hydrochloric acid in 20 ml of anhydrous ethanol and then, after the reaction medium has been left to stand for 4 days at 0° C., it is poured into 200 ml of anhydrous ether at 0° C., with stirring; the precipitate formed is filtered off, washed with ether and then dried under vacuum to give 25.8 g of the expected product.

B) Ethyl butyrimidate 16 g of the imidate obtained in step A are dissolved in 100 ml of dichloromethane and 50 ml of water, and 15 g of potassium carbonate are added. After decantation, the dichloromethane is dried over potassium carbonate and then evaporated off to dryness without heating.

C) Ethyl ester of 1-aminocyclohexane carboxylic acid

1-Aminocyclohexanecarboxylic acid is commercially available. 15 g of this amino acid are added at 0° C. to a solution of 23 g of gaseous hydrochloric acid in 150 ml of anhydrous ethanol. The reaction medium is refluxed for 5 hours and then concentrated to dryness and the residue is taken up in ether. The white solid obtained is filtered off, washed with ether and then dissolved in a mixture of 300 ml of ether and 100 ml of water. The pH is brought to 9 by the addition of a solution of potassium carbonate. The organic phase is decanted, washed with a saturated solution of sodium chloride, dried over sodium sulfate and then evaporated to dryness to give 14 g of the expected product in the form of an oil.

D) 2-n-Propyl-4-spirocyclohexane-2-imidazolin-5-one 14 g of the product obtained in step C are dissolved in 200 ml of xylene containing 0.6 ml of acetic acid. Half the imidate obtained in step B is added and the mixture is heated to the reflux point. After 1 and a half hours, half the remaining imidate is added and the last quarter is then added after 4 hours. After a total reflux time of 7 hours, the medium is evaporated to dryness. The solid obtained is taken up in hexane, filtered off, washed with ether and then dried.

This gives 10.3 g of the expected imidazolinone.

M.p.=124°-125° C. IR (CHCl₃): 1715 cm$^{-1}$: C=O 1635 cm$^{-1}$: C=N Note: The compound present in solution is indeed an imidazolin-5-one according to the values of the IR bands.

E) 2-n-Propyl-4-spirocyclohexane-1-[(2'-tert-butoxycarbonylbiphenyl-4-yl)methyl]-2-imidazolin-5-one 970 mg of the imidazolinone obtained in step D are added to 0.24 g of sodium hydride as an 80% dispersion in oil, suspended in 10 ml of dimethylformamide. After stirring for 20 minutes under nitrogen, 1.91 g of 4-bromomethyl-2'-tert-butoxycarbonylbiphenyl, prepared according to European patent application 324 377, are added over 5 minutes. After stirring for 1 hour, the medium is concentrated to half its volume under vacuum and taken up in 100 ml of ethyl acetate and then in 20 ml of water. The organic phase is decanted, washed with a saturated solution of sodium chloride, dried over sodium sulfate and then concentrated under vacuum. The residue is chromatographed on silica using an ethyl acetate/toluene mixture as the eluent to give 2.10 g of the expected product in the form of a wax.

IR (CHCl₃): 1705-1715 cm$^{-1}$: C=O, C=O (ester, imidazolinone) 1635 cm$^{-1}$: C=N Analysis of the NMR spectrum confirms the structure.

F) 1-[(2'-Carboxybiphenyl-4-yl)methyl]-2-n-propyl-4-spirocyclohexane-2-imidazolin-5-one (Example 20)

1.25 g of the tert-butyl ester obtained in step E are stirred for 45 minutes in a mixture of 11 ml of dichloromethane and 15 ml of trifluoroacetic acid. After concentration under vacuum, the residue is taken up in ether. The solid formed is filtered off, washed with ether and then dried to give 1.04 g of a white solid.

M.p.=170°-172° C. NMR spectrum: 7.10-7.80 ppm: m: 8H: aromatic protons 4.90 ppm: s: 2H: N—C$\underline{H}_2$—C₆H₄— 2.45 ppm: t: 2H: CH₃—CH₂—C$\underline{H}_2$— 1.40-1.80 ppm: m: 12H: spirocyclohexane+CH₃—C$\underline{H}_2$—CH₂— 0.90 ppm: t: 3H: C$\underline{H}_3$—CH₂—CH₂—

1.60 g of the trifluoroacetate obtained previously are dissolved in 150 ml of ethyl acetate and 20 ml of water. 1N sodium hydroxide solution is added to bring the pH to 5.0. The organic phase is decanted, washed with a saturated solution of sodium chloride, dried over sodium sulfate and then evaporated to dryness. The solid residue is taken up in ethyl ether, filtered off and dried.

m=1.14 g. M.p.=208°-210° C.

G) 1-[(2'-N-Cyanocarboxamidebiphenyl-4-yl)methyl]-2propyl-4-spirocyclohexane-2-imidazolin-5-one Example 21

0.54 ml of thionyl chloride is added to 300 mg of the compound prepared in the previous step, suspended in 5 ml of DCM. After 1 and a half hours, the reaction medium is concentrated under vacuum and then evaporated twice with benzene. The acid chloride thus obtained is dissolved in 2 ml of dioxane and added to a solution of 42 mg of cyanamide in 1 ml of dioxane containing 0.2 ml of 10N sodium hydroxide solution. After 1 and a half hours, the reaction medium is diluted with 150 ml of ethyl acetate and 20 ml of water, the pH is brought to 5 with acetic acid and the organic phase is decanted, washed with a saturated solution of sodium chloride, dried over sodium sulfate and then evaporated to dryness. The residue is chromatographed on silica using a chloroform/methanol/acetic acid mixture (90/8/2; v/v) as the eluent to give 160 mg of the expected product in the form of a solid.

IR (KBr): 2150 cm$^{-1}$: C≡N Mass spectrum: MH$^-$: 429 NMR spectrum: 7.20-7.70 ppm: m: 8H: aromatic protons 4.75 ppm: s: 2H: N—C$\underline{H}_2$—C₆H₄— 2.40 ppm: t: 2H: CH₃—CH₂—C$\underline{H}_2$— 1.30-1.80 ppm: m: 12H: CH₃—C$\underline{H}_2$—CH₂— and spirocyclohexane 0.85 ppm: t: 3H: C$\underline{H}_3$—CH₂—CH₂

EXAMPLE 22

1-[(2'-(N-4-carboxy-1,3-thiazol-2-ylacetamide)-biphenyl-4-yl)methyl]-2-n-propyl-4-spirocyclohexane-2-imidazolin-5-one

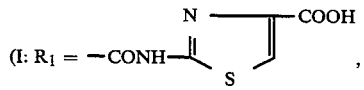

(I: R₁ = —CONH—

R₂ = H, R₃ = n-C₃H₇,
CR₄R₅ = cyclohexane, X = O)

This compound is prepared from the compound obtained in Example 20.

2-Amino-4-ethoxycarbonyl-1,3-thiazole is prepared according to B. Plouvier et al., J. Heterocycl. Chem., 1989, 26(6), 1646.

A) 1-[N-4-carbethoxy-1,3-thiazol-2-ylacetamide)-2'-biphenyl-4-ylmethyl]-2-n-propyl-4-spirocyclohexane-2-imidazolin-5-one (sic)

500 mg of BOP and 0.14 ml of triethylamine are added to a solution of 404 mg of the compound prepared in Example 20 and 190 mg of thiazole derivative in 4 ml of DCM and 1 ml of DMF. The mixture is stirred for 40 hours at room temperature and then 7 hours at 50° C. The reaction medium is taken up in 50 ml of ethyl acetate and washed twice with a KHSO₄—K₂SO₄ solution, then twice with a saturated solution of sodium bicarbonate and then once with a saturated solution of sodium chloride. After drying over sodium sulfate, the organic phase is concentrated under vacuum and the residue is chromatographed on silica using an ethyl acetate/toluene mixture as the eluent to give 120 mg of the expected product.

M.p.=96°-98° C.

B)

0.5 ml of 2N sodium hydroxide solution is added to 110 mg of the product obtained in the previous step, dissolved in 1 ml of methanol and 1 ml of dioxane. After stirring for 35 minutes, the reaction medium is diluted with 10 ml of water and 60 ml of ethyl acetate and the pH is brought to 5 by the addition of 1N hydrochloric acid. The organic phase is decanted, washed with a saturated solution of sodium chloride, dried over sodium sulfate and then concentrated. The residue is taken up in ether, filtered off and dried.

m=100 mg. M.p.=145°-148° C. NMR spectrum: 8.0 ppm: s: 1H: H in the 5 position of the thiazole 7.1-7.7 ppm: m: 8H: aromatic protons 4.7 ppm: s: 2H: N—C$\underline{H}$ 2—C₆H₄— 2.25 ppm: t: 2H: C$\underline{H}_2$—CH₂—CH₃ 1.2–1.8 ppm: m: 12H: cyclohexane and C$\underline{H}_2$—C$\underline{H}_2$—CH₃ 0.85 ppm: t: 3H: CH₂—CH₂—C$\underline{H}_3$

EXAMPLE 23

2-n-Butyl-1-[(2'-(2-cyanoguanidinocarbonyl)biphenyl-4-yl)methyl]-4-spirocyclopentane-2-imidazolin-5-one

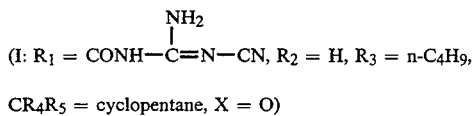

(I: R₁ = CONH—C=N—CN, R₂ = H, R₃ = n-C₄H₉,

CR₄R₅ = cyclopentane, X = O)

The acid chloride of the compound obtained in Example 2 is prepared. 1 g of this compound is placed in 20 ml of DCM, in the presence of 1.8 ml of thionyl chloride, and the mixture is stirred at room temperature for 2 hours. After concentration of the medium, the residue is taken up in benzene and the mixture is then concentrated again. The crude product isolated is then used. It is mixed with 417 mg of dicyanodiamide, 0.5 ml of 10N sodium hydroxide solution, 0.5 ml of water and 10 ml of dioxane and the mixture is then stirred for 5 hours. The reaction medium is taken up in water and ethyl acetate, potassium carbonate is added and the mixture is then concentrated. The residue obtained is chromatographed on silica using a DCM/methanol mixture (95/5; v/v) as the eluent. 100 mg of the expected product are isolated. M.p.=105° C.

EXAMPLE 24

4-Benzylidene-2-n-butyl-1-[(2'-carboxybiphenyl-4-yl)methyl]-2-imidazolin-5-one trifluoroacetate , (I: R₁=CO₂H, R₂=H, R₃=n-C₄H₉,
R₄R₅==CH—C₆H₅, X=O)

A) Tert-butyl 4-( 1-benzylidene-1-valerylaminomethylamidomethyl)biphenyl-2-carboxylate

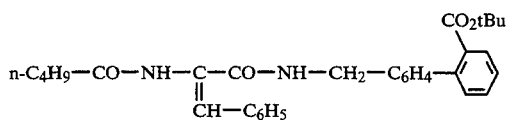

Starting from N-Boc-α-dehydro-(L)-phenylalanine, the N-carboxyanhydride of α-dehydro-(L)-phenylalanine is prepared according to R. Jacquier et al., Tetrahedron Lett., 1984, 25(26), 2775. p. 644 mg of tert-butyl 4-aminomethylbiphenyl-2'-carboxylate are added to a solution of 430 mg of this compound in 5 ml of THF, the mixture is stirred for 2 hours at room temperature, 1 ml of methyl orthovalerate is then added and the mixture is evaporated to dryness under vacuum without heating. The residue is heated for 3 hours at 100° C., concentrated under vacuum and then chromatographed on silica using a hexane/ethyl acetate mixture (4/1; v/v) as the eluent to give 580 mg of a white solid.

M.p.=154° C. NMR spectrum: 1.3 ppm: s: 9H: tBu 0.65 ppm: t: 3H: CH₃ (nBu) 2 ppm: t: 2H: CH₃—CH₂—C$\underline{H}_2$—CH₂—CO 4.4 ppm: d: 1H: C$\underline{H}_2$—NH 6.8 ppm: s: 1H: C$\underline{H}$ (=CH—C₆H₅)

B) 4-Benzylidene-2-n-butyl-1-[(2'-tert-butoxycarbonylbiphenyl-4-yl)methyl]-2-imidazolin-5-one 440 mg of the compound obtained in step A are dissolved in 1 ml of acetic acid and heated for 30 minutes at 100° C.

The solution is evaporated to dryness under vacuum and the residue is chromatographed on silica using a hexane/ethyl acetate mixture (4/1; v/v) as the eluent to give 130 mg of the expected product in the form of an oil.

NMR spectrum: 4.9 ppm: s: 2H: CH₂ (N—C$\underline{H}_2$—C₆-H₄—)

C)

100 mg of the compound obtained in the previous step are dissolved in 1 ml of DCM, 1 ml of trifluoroacetic acid is added and the mixture is then stirred for 40 minutes at room temperature and evaporated under vacuum. The residue is taken up several times in DCM and then evaporated. A white solid precipitates on the addition of ethyl ether.

m=101 mg. M.p.=85° C. Mass spectrum: MH+: 439 NMR spectrum: 0.82 ppm: t: 3H: CH₃ (nBu) 1.3 ppm: sext: 2H: CH₃—C$\underline{H}_2$— 1.6 ppm: m: 2H: CH₃—CH-₂—C$\underline{H}_2$— 2.6 ppm: t: 2H: CH₃—CH₂—CH₂—C$\underline{H}_2$— 4.82 ppm: s: 2H: C$\underline{H}_2$—C₆H₄— 7.05 ppm: s: 1H: =C$\underline{H}$—C₆H₅ 7.2–8.2 ppm: m: 13H: aromatic protons

EXAMPLE 25

4-Benzylidene-1-[(2'-carboxybiphenyl-4-yl)methyl]-2-phenyl-2-imidazolin-5-one (I: R₁=CO₂H, R₂=H, R₃=C₆H₅,
R₄R₅==CH—C₆H₅, X=O)

A) 4-Benzylidene-2-phenyloxazol-5-one 1.8 g of hippuric acid and 0.4 g of potassium bicarbonate are dissolved in 4 ml of acetic anhydride, the solution is heated for a few minutes at 50° C. and then cooled to room temperature and 1.49 g of benzaldehyde are added. After 1 hour at room temperature, 20 ml of distilled water are added at 80° C. The solid which precipitates is filtered off, washed with water and ethanol and then dried to give 1.24 g of the expected product in the form of a yellow solid.

M.p.=215° C. NMR spectrum: 7.4 ppm: s: 1H: =C$\underline{H}$—C₆H₅ 8.1–8.4 ppm: m: 10H: aromatic protons B) Tert-butyl 4-(1-benzoylamino-1-benzylidenemethylamidomethyl)biphenyl-2'-carboxylate A mixture containing 500 mg of the compound obtained in the previous step, 570 mg of tert-butyl 4-aminomethylbiphenyl-2'-carboxylate and 10 ml of pyridine is heated at 110° C. for 3 hours. It is evaporated under vacuum, the residue is taken up in chloroform and the mixture is then evaporated again. The residue is chromatographed on silica using a hexane/ethyl acetate mixture (3/1 then 2/1; v/v) as the eluent to give 106 mg of the expected product in the form of a yellow solid.

NMR spectrum: 1.1 ppm: s: 9H: tBu 4.35 ppm: t: 2H: —C$\underline{H}_2$—NH 7.05–7.06 ppm: m: 19H: aromatic protons+C₆H₅—C$\underline{H}$= 8.65 ppm: t: 1H: N$\underline{H}$—CH₂ 9.9ppm: s: 1H: N$\underline{H}$—CH=

C)

A mixture of 1.2 g of the compound obtained in the previous step and 1.1 g of freshly melted sodium acetate is refluxed for 6 hours in 5 ml of acetic acid. It is left to cool and an insoluble material is then precipitated by the addition of chloroform. The filtrate is evaporated and the residue is chromatographed on silica using a chloroform/methanol mixture (98/2; v/v) as the eluent. The solid obtained is recrystallized from ethyl ether.

m=692 mg. M.p.=120° C. NMR spectrum: 4.95 ppm: s: 2H: C$\underline{H}_2$—C$_6$H$_4$— 7.1-8.3 ppm: m: 19H: aromatic protons +=C$\underline{H}$—C$_6$H$_5$

EXAMPLES 26 AND 27

2-n-Butyl-1-[(2'-(2-methyltetrazol-5-yl)biphenyl-4-yl)methyl]-4-spirocyclopentane-2-imidazolin-5-one (Example 26) and 2-n-butyl-1-[(2'-(1-methyltetrazol-5-yl)biphenyl-4-yl)methyl]-4-spirocyclopentane-2-imidazolin-5-one (Example 27)

In 10 ml of DMF, 500 mg of the compound prepared in Example 5 are mixed with 58 mg of sodium hydride, the mixture is stirred for 30 minutes, 179 mg of methyl iodide and 2 ml of DMF are then added and the mixture is stirred at room temperature for 4 hours. The reaction medium is concentrated and the concentrate is taken up in water and then extracted with ethyl acetate. The extract is dried over sodium sulfate and filtered and the solvent is evaporated off. The residue is chromatographed on silica using a hexane/ethyl acetate mixture (6/4; v/v) as the eluent. 2 fractions are isolated:

90 mg of the compound of Example 26 and
184 mg of the compound of Example 27

NMR spectra:

Example 26 0.7 ppm: t: 3H: CH$_3$— (nBu) 1.2 ppm: sext: 2H: CH$_3$—C$\underline{H}_2$— 1.4 ppm: quint: 2H: CH$_3$—CH$_2$—C$\underline{H}_2$— 1.5-1.9 ppm: m: 8H: cyclopentane 2.25 ppm: t: 2H: CH$_3$—CH$_2$—C$\underline{H}_2$—CH$_2$— 4.15 ppm: s: 3H: N—CH$_3$ 4.6 ppm: s: 2H: —N—C$\underline{H}_2$—C$_6$H$_4$— 7 ppm, AA', BB' system: 4H: CH$_2$—C$_6$$\underline{H}_4$— 7.3-7.75 ppm: m: 4H: CH$_2$—C$_6$H$_4$—C$_6$$\underline{H}_4$—

Example 27 0.7 ppm: t: 3H: CH$_3$ (nBu) 1.15 ppm: sext: 2H: CH$_3$—C$\underline{H}_2$— 1.38 ppm: quint: 2H: CH$_3$—CH$_2$—C$\underline{H}_2$— 1.5-1.9 ppm: m: 8H: cyclopentane 2.2 ppm: t: 2H: CH$_3$—CH$_2$—CH$_2$—C$\underline{H}_2$— 3.35 ppm: s: 3H: N—CH$_3$ 4.6 ppm: s: 2H: N—C$\underline{H}_2$—C$_6$H$_4$ 7 ppm: AA', BB' system: 4H: N—C$\underline{H}_2$—C$_6$H$_4$— 7.4-7.8 ppm: m: 4H: CH$_2$—C$_6$H$_4$—C$_6$$\underline{H}_4$—

EXAMPLE 28

2-n-Butyl-6-spirocyclopentane-3-[(2'-(tetrazol-5-yl)biphenyl-4-yl)methyl]-4(1H)-5,6-dihydropyrimidin-4-one A) Ethyl cyclopentylideneacetate 6 g of 80% sodium hydride are placed in 40 ml of benzene, and 57.1 ml of ethyl triethylphosphonoacetate are added dropwise at a temperature below 35° C. After 1 hour at room temperature, 24.3 ml of cyclopentanone are added dropwise. The mixture is heated at 65° C. for 15 minutes and then cooled to room temperature and the supernatant liquor is decanted. 25 ml of benzene are added, the mixture is heated at 65° C. for 15 minutes, cooled and decanted and the supernatant liquor is then recovered. The operation is repeated once. Evaporation of the liquors gives 42 g of the expected product, which is distilled.

B.p.=102° C. under 11 mm of mercury.
m=22.8 g.

B) (1-Aminocyclopentyl)acetamide 150 ml of gaseous ammonia are added to 20 g of the ethyl cyclopentylideneacetate prepared previously and the mixture is heated at 150° C. for 72 hours. The product obtained after evaporation is purified by chromatography on silica using a DCM/methanol/20% aqueous ammonia mixture (90/10/1; v/v/v) as the eluent. The product obtained is dissolved in DCM and the solution is dried over sodium sulfate. It is filtered and the DCM is evaporated off to give 7.2 g of the expected product.

C) 2-n-Butyl-6-spirocyclopentane-4(1H)-5,6-dihydropyrimidin-4-one

A mixture containing 4.57 g of the (1-aminocyclopentyl)acetamide prepared previously, 25 ml of methyl orthovalerate and a few drops of acetic acid is heated at 100° C. for 18 hours. After evaporation of the excess orthovalerate, the residue is taken up in an ethyl acetate/sodium bicarbonate mixture, then washed with an aqueous solution of sodium chloride, dried over sodium sulfate and then purified by chromatography on silica using a DCM/methanol mixture (98/2; v/v) as the eluent.

m=5 g. NMR spectrum: 0.75 ppm: t: 3H: CH$_3$ (nBu) 1.2 ppm: sext: 2H: CH$_3$—C$\underline{H}_2$— 1.3-1.8 ppm: m: 10H: CH$_3$—CH$_2$—C$\underline{H}_2$ and cyclopentane 2 ppm: t: 2H: CH$_3$—CH$_2$—C$\underline{H}_2$—CH$_2$— 2.15 ppm: s: 2H: C$\underline{H}_2$—CO 9.95 ppm: sb: 1H: N$\underline{H}$ This compound is the one obtained in Example 10, step C.

D) 2-n-Butyl-6-spirocyclopentane-3-[(2'-triphenylmethyltetrazol-5-yl)biphenyl-4-yl-methyl]-4(1H)-5,6-dihydropyrimidin-4-one 327 mg of 80% sodium hydride in 30 ml of DMF are mixed for 30 minutes under nitrogen with 1.5 g of the pyrimidinone prepared previously, and 5.27 g of 4-bromomethyl-2'-(triphenylmethyltetrazol-5-yl)biphenyl are added. After stirring for 4 hours at room temperature, the solvents are evaporated off and the residue is taken up in ethyl acetate and water, dried over sodium sulfate and concentrated. The product obtained is purified by chromatography on silica using an ethyl acetate/hexane mixture (3/7; v/v) as the eluent.

m=3.2 g.

E)

3 g of the compound obtained in the previous step are placed in 15 ml of methanol, the mixture is cooled in a water/ice bath, 2.2 ml of 4N HCl are added and the mixture is stirred for 5 hours at room temperature. After evaporation, the residue is taken up in ethyl acetate and water, and sodium hydroxide solution is then added to give a basic pH (pH 11). The mixture is left to decant and the aqueous phase is washed with ethyl ether and toluene and then ether again. This aqueous phase is brought to pH 5 by the addition of dilute hydrochloric acid and is then extracted with ethyl acetate and the extract is dried and concentrated. The product obtained is purified on silica using a DCM/methanol mixture (95/5; v/v) as the eluent to give 800 mg of the expected product.

NMR spectrum: 0.85 ppm: t: 3H: CH$_3$ (nBu) 1.30 ppm: sext: 2H: CH$_3$—C$\underline{H}_2$ 1.40-1.95 ppm: m: 10H: cyclopentane and CH$_2$—C$\underline{H}_2$—CH$_2$—CH$_3$ 2.30 ppm: t: 2H: CH$_2$—CH$_2$—CH$_2$—CH$_3$ 2.55 ppm: s: 2H: C$\underline{H}_2$—CO 4.95 ppm: s: 2H: N—C$\underline{H}_2$—C$_6$H$_4$— 7.05 ppm: m: 4H: CH$_2$—C$_6$$\underline{H}_4$— 7.55-7.82 ppm: m: 4H: CH$_2$—C$_6$H$_4$—C$_6$$\underline{H}_4$—

EXAMPLE 29

2-n-Butyl-3-[(2'-carboxybiphenyl-4-yl)methyl]-5-spirocyclopentane-5(1H)-5,6-dihydropyrimidin-4-one trifluoroacetate A) Ethyl 1-cyanocyclopentanecarboxylate This compound is prepared according to Helv. Chim. Acta, 1952, 35(7), 2561.

9.2 g of sodium are dissolved in 200 cm$^{-3}$ of absolute ethanol. Half the solution of sodium ethylate formed is poured into a funnel. 24.88 g of ethyl cyanoacetate are added to the remaining half and the mixture is brought to the reflux point.

43.19 g of 1,4-dibromobutane are poured into another funnel and the solution of sodium ethylate and the 1,4-dibromobutane are simultaneously added dropwise to the reaction medium. When the addition is complete, reflux is maintained for 2 hours. The mixture is evaporated and the residue is taken up in an ethyl ether/water mixture, washed with a saturated solution of sodium chloride and then dried. The product obtained distils at 115°–120° C. under 11 mm of mercury.

m=24 g.

B) Ethyl 1-aminomethylcyclopentanecarboxylate

This compound is prepared by the catalytic hydrogenation of ethyl 1-cyanocyclopentanecarboxylate.

20 g of ethyl 1-cyanocyclopentanecarboxylate are placed in 200 ml of a 10% solution of ammonia in ethanol and hydrogenated at 60° C. under a pressure of 100 bar in the presence of rhodium-on-alumina for 72 hours. After filtration on cellite ®—and evaporation, the residue is chromatographed on silica using a DCM/methanol/20% aqueous ammonia mixture (98/2/0.5; v/v/v) as the eluent.

m=12.8 g.

C)   2-n-Butyl-5-spirocyclopentane-4(1H)-5,6-dihydropyrimidin-4-one

A mixture containing 13.12 g of the compound obtained in the .previous step and 13.5 g of ethyl valerimidate in 100 ml of xylene containing a few drops of acetic acid is refluxed for 13 hours. The reaction medium is evaporated and the residue is taken up in ethyl acetate and a 10% solution of sodium carbonate and then dried and concentrated.

m=14 g. M.p.=89°–91° C. NMR spectrum: 0.80 ppm: t: 3H: CH$_3$ (nBu) 1.10–1.80 ppm: m: 12H: CH$_3$—CH$_2$—CH$_2$— and cyclopentane 2.05 ppm: t: 2H: CH$_3$—C$\underline{H}_2$—C$\underline{H}_2$—CH$_2$— 3.20 ppm: s: 2H: CH$_2$ (pyrimidinone) 10 ppm: 1H: s: NH—CO D) 2-n-Butyl-5-spirocyclopentane-3-[(2'-tert-butoxycarbonylbiphenyl-4-yl)methyl]-4(1H)-5,6-dihydropyrimidin-4-one 500 mg of the product obtained in the previous step are placed in 40 ml of DMF in the presence of 115 mg of an 80% dispersion of sodium hydride in oil, under argon, and stirred at room temperature for half an hour. 1.08 g of 4-bromomethyl-2'-tert-butoxycarbonylbiphenyl are added and the mixture is stirred for 2 hours. After evaporation, the residue is taken up in an ethyl acetate/water mixture, washed with a saturated solution of sodium chloride and then dried, concentrated and chromatographed on silica using an ethyl acetate/hexane mixture (3/7; v/v) as the eluent.

m=280 mg.

E)

250 ml of the tert-butyl ester prepared in the previous step are dissolved in 10 ml of DCM. The solution is cooled in a bath of iced water, 5 ml of cold trifluoroacetic acid are then added and the mixture is stirred for one hour in the cold and then 1 hour at room temperature. It is evaporated under reduced pressure. The residue is taken up in ethyl ether and then evaporated. The operation is repeated 3 times, the evaporation residue is then taken up in hexane and triturated and the hexane is then decanted. The product is taken up in ethyl ether and the precipitate is filtered off.

m=190 mg. M.p.=153°–155° C. NMR spectrum: 0.85 ppm: t: 3H: CH$_3$ (nBu) 1.35 ppm: sext: 2H: CH$_3$—CH$_2$— 1.45–2.20 ppm: m: 10H: CH$_3$—CH$_2$—CH$_2$— and cyclopentane 2.80 ppm: t: 2H: CH$_3$—CH$_2$—CH$_2$—C$\underline{H}_2$— 3.80 ppm: s: 2H: CH$_2$ (pyrimidinone) 5.15 ppm: s: 2H: N—CH$_2$— 7.25 ppm: m: 8H: aromatic protons

TABLE 1

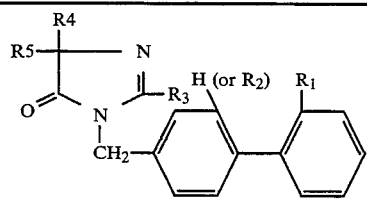

(I)

| (Ex.) | R$_1$ | R$_3$ | CR$_4$R$_5$ | Salt | M.p. °C. |
|---|---|---|---|---|---|
| (30) | CO$_2$H | n-C$_4$H$_9$ | cyclohexane | TFA | 172–174 |
| (31) | CO$_2$CH$_3$ | n-C$_4$H$_9$ | cyclopentane | — | 86–87 |
| (32)* | CO$_2$H | n-C$_4$H$_9$ | C(CH$_3$)C$_6$H$_5$ | TFA | 55–60 |
| (33) | CO$_2$H | n-C$_4$H$_9$ | C(C$_2$H$_5$)$_2$ | TFA | 82–84 |
| (34) | CO$_2$H | n-C$_3$H$_7$ | cyclopentane | TFA | 164 |
| (35) | ** | n-C$_4$H$_9$ | cyclopentane | — | 163–164 |
| (36) | CO$_2$H | C$_6$H$_5$ | cyclopentane | TFA | 178 |
| (37) | CO$_2$H | n-C$_4$H$_9$ | cycloheptane | TFA | 160–162 |
| (38) | CO$_2$H | CH$_3$ | cyclopentane | TFA | 140 |
| (39) | CO$_2$H | n-C$_4$H$_9$ | cyclopropane | — | 204–205 |
| (40) | tetrazol-5-yl | —CH$_2$—CH$_2$—CH=CH$_2$ | cyclopentane | — | 110 |
| (41) | tetrazol-5-yl | n-C$_4$H$_9$ | cyclohexane | — | 130 |
| (42) | tetrazol-5-yl | n-C$_3$H$_7$ | cyclohexane | — | 141 |
| (43) | CO$_2$H | cyclopentyl | cyclopentane | TFA | 82–88 |
| (44) | CO$_2$H | n-C$_5$H$_{11}$ | cyclopentane | TFA | 151 |
| (45) | CO$_2$H | CH$_2$—C$_6$H$_5$ | cyclopentane | TFA | 88 |
| (46) | CO$_2$H | H | cyclopentane | — | 230 |
| (47) | CO$_2$H | n-C$_4$H$_9$ | cyclobutane | TFA | 178 |
| (48) | CO$_2$H | n-C$_4$H$_9$ | cyclododecane | TFA | 130–135 |
| (49) | CO$_2$H | n-C$_4$H$_9$ | 2-adamantane | TFA | 164–166 |
| (50) | CO$_2$H | n-C$_4$H$_9$ | 4-phenyl-cyclohexane | TFA | 155–157 |
| (51) | CO$_2$H | n-C$_4$H$_9$ | 4-methyl-cyclohexane | TFA | 198–200 |
| (52) | CO$_2$H | n-C$_4$H$_9$ | N-acetal-4-piperidine | TFA | 90–95 |

TABLE 1-continued (I)

| (Ex.) | $R_1$ | $R_3$ | $CR_4R_5$ | Salt | M.p. °C. |
|---|---|---|---|---|---|
| (53) | $CO_2H$ | $C_3F_7$ | cyclopentane | — | 141–143 |
| (54)* | $CO_2H$ | n-$C_4H_9$ | C($CH_3$)-(phenyl)-$CF_3$ | — | 207–209 |
| (55)* | $CO_2H$ | n-$C_4H_9$ | C($CH_3$)-(phenyl)-Cl | TFA | 105 |
| (56) | $CO_2H$ | n-$C_4H_9$ | (piperidine)-N—CO—$CF_3$ | TFA | 95–105 |
| (57) | $CO_2H$ | n-$C_4H_9$ | (piperidine)-N—CO—CH($NH_2$)—CH($C_2H_5$)—$CH_3$ | TFA | 125–135 |
| (58) | $CO_2H$ | n-$C_4H_9$ | (piperidine)-N—CO—$C_6H_5$ | TFA | 85–90 |

**$R_1$ = H and $R_2$ = $CO_2H$
*These compounds have an asymmetric carbon and are isolated in the form of a mixture of optical isomers.

EXAMPLE 59

(R,S)-2-n-Butyl-1-[(2'-carboxybiphenyl-4-yl)methyl]-4-cyclohexyl-4-methyl-2-imidazolin-5-one trifluoroacetate A) 5-Cyclohexyl-5-methylhydantoin This compound is prepared according to J. Org. Chem., 1960, 25, 1920–1924.

A solution of 50 g of cyclohexyl methyl ketone in 400 ml of 95° alcohol is added over 30 minutes to 29.4 g of sodium cyanide and 192 g of ammonium carbonate in 400 ml of water. The mixture is heated at 55°–60° C. for 4 hours and then evaporated to half its volume under vacuum and left to stand overnight at +4° C. The precipitate formed is filtered off, washed with water and then dried under vacuum over phosphorus pentoxide to give 65.5 g of the expected hydantoin, which is identified by its IR and NMR spectra.

M.p.=220° C.

B) (R,S)-2-Amino-2-cyclohexylpropionic acid

This compound is prepared according to J. Org. Chem., 1960, 25, 1920–1924.

A mixture containing 7 g of the hydantoin prepared in the previous step and 28 g of barium hydroxide octahydrate in 150 ml of water is heated at 160° C. for 5 hours in a steel tube. The reaction medium is saturated with dry ice, the insoluble material formed is filtered off and the filtrate is then concentrated under vacuum. The solid residue is taken up in acetone, filtered off and dried to give 5.25 g of the expected acid, which is identified by its IR and NMR spectra. The product melts at 350° C. with decomposition.

C) Ethyl ester of (R,S)-2-amino-2-cyclohexylpropionic acid 3 g of the acid prepared in the previous step are added to 40 ml of absolute alcohol saturated with gaseous hydrochloric acid and the mixture is then refluxed for 20 hours, with stirring. The reaction medium is evaporated under vacuum and the residue is taken up in an ether/water mixture, which is brought to pH 9 by the addition of a saturated solution of sodium bicarbonate. The organic phase is decanted, washed with a saturated solution of sodium chloride and then evaporated under vacuum to give 2.1 g of the expected ester in the form of an oil. Identification by IR and NMR spectra.

D) Ethyl valerimidate

This compound is prepared in the form of the hydrochloride according to Mac Elvain (J. Amer. Chem. Soc., 1942, 64, 1825–1827). It is freed from its hydrochloride by reaction with potassium carbonate and then extracted with DCM.

E) (R,S)-2-n-Butyl-4-cyclohexyl-4-methyl-2-imidazolin-5-one 2 g of the ester prepared in step C and 2.35 g of ethyl valerimidate are mixed in 6 ml of xylene, to which 6 drops of acetic acid are added; the reaction medium is refluxed for 6 hours. It is then concentrated under vacuum and the residue is chromatographed on fine silica gel using a chloroform/methanol/acetic acid mixture (95/9/3; v/v/v) as the eluent. The fractions containing the desired product are combined and then evaporated under vacuum; the residue is taken up in an ethyl acetate/water mixture and the pH is brought to 9 by the addition of a solution of sodium hydroxide. The organic phase is decanted, washed with water and then with a saturated solution of sodium chloride, dried over sodium sulfate and then evaporated to dryness. The expected product is obtained in the form of a thick oil, which solidifies to give an amorphous solid.

m=1.56 mg. IR (chloroform): 1720 cm$^{-1}$: C=O 1640 cm$^{-1}$: C=N NMR consistent.

F) 4-Bromomethyl-2'-tert-butoxycarbonylbiphenyl

This compound is prepared by the method described in European patent application 324 377.

G) (R,S)-2-n-Butyl-4-cyclohexyl-4-methyl-1-[(2'-tert-butoxycarbonylbiphenyl-4-yl)methyl]-2-imidazolin-5-one 1.5 g of the imidazolinone prepared in the previous step are dissolved in 20 ml of DMF. 250 mg of sodium hydride as an 80% dispersion in oil are added. After stirring for 20 minutes, 2.48 g of the compound prepared in step F) are added and the reaction medium is left to stand for 2 hours at RT. It is taken up in an ethyl acetate/water mixture; the organic phase is decanted, washed with water and with a saturated solution of sodium chloride, dried over sodium sulfate and then concentrated under vacuum. The residue is chromatographed on silica using an ethyl acetate/toluene mixture (1/4; v/v) as the eluent to give 1.8 g of the expected product in the form of a white wax.

IR (chloroform): 1710-1730 cm$^{-1}$: ester and imidazolinone C=O 1630 cm$^{-1}$: C=N H) (R,S)-2-n-Butyl-1-[(2'-carboxybiphenyl-4-yl)methyl]-4-cyclohexyl-4-methyl-2-imidazolin-5-one trifluoroacetate 1.5 g of the compound obtained in the previous step are stirred for 40 minutes in 7 ml of TFA and 7 ml of DCM. The reaction medium is concentrated under vacuum and taken up in ether to give a white solid, which is filtered off, washed with ether and dried under vacuum.

m=1.40 g. M.p.=171° C. MH+: 447. NMR: 7.10–7.70 ppm: m: 8 aromatic H 4.45 ppm: s: 2H: N—CH$_2$—C$_6$H$_4$— 2.25 ppm: s: CH$_3$ in the 4 position

EXAMPLE 60

(R,S)-2-n-Butyl-1-[(2'-carboxybiphenyl-4-yl)methyl]-4-cyclohexylmethyl-4-methyl-2-imidazolin-5-one trifluoroacetate The following compounds are prepared from cyclohexyl methyl ketone according to the procedures described in Example 59:

A) 5-Cyclohexylmethyl-5-methylhydantoin
M.p.=205°–206° C.

B) (R,S)-2-Amino-3-cyclohexyl-2-methylpropionic acid
Characterized by its IR and NMR spectra.

C) Ethyl ester of (R,S)-2-amino-3-cyclohexyl-2-methylpropionic acid
Characterized by its IR and NMR spectra.

D) (R,S)-2-n-Butyl-4-cyclohexylmethyl-4-methyl-2-imidazolin-5-one

This product is obtained in the form of an oil, which solidifies. Identification by IR and NMR.

IR (chloroform): 1720 cm$^{-1}$: imidazolinone C=O 1630 cm$^{-1}$: C=N

E) (R,S)-2-n-Butyl-4-cyclohexylmethyl-4-methyl-1-[(2'-tert-butoxycarbonylbiphenyl-4-yl)methyl]-2-imidazolin-5-one This product is obtained by treating the compound of step D with 4-bromomethyl-2'-tert-butoxycarbonylbiphenyl in the presence of sodium hydride. After purification by chromatography, the product is in the form of an oil, which crystallizes in the refrigerator.

Yield: 51%. M.p.=73°–75° C. IR (KBr): 1700–1730 cm$^{-1}$: imidazolinone and ester C=O 1630 cm$^{-1}$: C=N F) (R,S)-2-n-Butyl-1-[(2'-carboxybiphenyl-4-yl)methyl]4-cyclohexylmethyl-4-methyl-2-imidazolin-5-one trifluoroacetate Yield: 90%. M.p.=143°–146° C. NMR: 7.20–7.80 ppm: 8H: aromatic protons 4.85 ppm: m: 2H: N—C$\underline{H}$$_2$—C$_6$H$_4$— 2.70 ppm: t: 3H: —CH$_2$—CH$_2$—CH$_2$—C$\underline{H}$$_3$ 1.80–0.85 ppm: m: 20H: 4-methyl 4-cyclohexylmethyl —CH$_2$—CH$_2$—CH$_2$—CH$_3$ 0.80 ppm: t: 3H: CH$_2$—CH$_2$—CH$_2$—C$\underline{H}$$_3$

EXAMPLE 61

(R,S)-2-n-Butyl-1-[(2'-carboxybiphenyl-4-yl)methyl]-4-cyclohexyl-4-ethyl-2-imidazolin-5-one trifluoroacetate A) (R,S)-2-Amino-2-cyclohexylbutyronitrile hemioxalate 1.18 g of ammonium chloride and 1.5 ml of a 32% aqueous solution of ammonia are added successively to a solution of 1.03 g of sodium cyanide in 6 ml of water, followed, over 15 minutes, by 2.8 g of cyclohexyl ethyl ketone in 5 ml of methanol, and the reaction medium is heated at 60° C. for 6 hours. It is cooled and extracted 4 times with DCM and the extracts are then evaporated under vacuum. The residue is treated again with the same amounts of cyanide, ammonium chloride, aqueous ammonia, water and methanol at 60° C. for 6 hours. The reaction medium is then cooled and extracted 4 times with DCM and the extracts are dried and then evaporated under vacuum. The residue is taken up in 30 ml of acetone, and a solution of 1.1 g of oxalic acid dihydrate in 10 ml of acetone is added dropwise. After 15 minutes, the precipitate formed is filtered off, washed with acetone and then with ether and dried under vacuum to give 2.87 g of product, which becomes pasty at 120° C. Identification by IR and NMR.

IR of the free base: 2220 cm$^{-1}$: C≡N

B) (R,S)-2-Amino-2-cyclohexylbutyramide 2.84 g of the nitrile obtained in step A are added over 30 minutes to 6 ml of pure sulfuric acid. The mixture is heated for 1 hour at 85° C. and then 30 minutes at 100° C. After cooling, the reaction medium is added dropwise to 20 ml of iced 32% aqueous ammonia. The mixture is extracted with chloroform and the extract is then dried over sodium sulfate and evaporated under vacuum to give 2.5 g of the expected product in the form of a wax. Identification by IR and NMR.

C) (R,S)-2-n-Butyl-4-cyclohexyl-4-ethyl-2-imidazolin-5-one 2.45 g of the product obtained in the previous step are dissolved in 30 ml of THF; 1.84 ml of triethylamine are added, followed, over 25 minutes, by a solution of 1.73 ml of valeroyl chloride in 10 ml of THF. After stirring for 2 hours, 3.57 g of potassium hydroxide pellets, then 4 ml of water and then 10 ml of methanol are added and the mixture is refluxed for 3 hours. After cooling, 6 g of ammonium chloride are added and the reaction medium is concentrated to half its volume and then extracted with ethyl acetate. The organic phase is washed with a saturated solution of sodium chloride, dried over sodium sulfate and then concentrated under vacuum. The residue is taken up in 10 ml of hexane and left to stand for 4 hours at 0° C. The solid formed is filtered off and dried.

m=2.62 g. M.p.=80°-85° C. Identification by NMR and IR (chloroform and KBr).

D) (R,S)-2-n-Butyl-1-[(2'-tert-butoxycarbonylbiphenyl-4-yl)methyl]-4-cyclohexyl-4-ethyl-2-imidazolin-5-one The procedure described in Example 59, step G), is followed; 1.50 g of the expected product are obtained, after chromatography, by treating 1 g of the product of step C) with 4-bromomethyl-2'-tert-butoxycarbonylbiphenyl.

IR (chloroform): 1700-1720 cm$^{-1}$; imidazolinone and ester C=O 1635 cm$^{-1}$; C=N E) (R,S)-2-n-Butyl-1-[(2'-carboxybiphenyl-4-yl)methyl]-4-cyclohexyl-4-ethyl-2-imidazolin-5-one trifluoroacetate The expected product is obtained by treating the compound obtained in the previous step by the method described in Example 59, step H).

Yield: 85%. M.p.=159°-161° C. NMR: 7.10-7.70 ppm: m: 8H: aromatic protons 4.75 ppm: s: 2H: —N—$\underline{CH_2}$—C$_6$H$_4$— 2.60 ppm: t: 2H: —$\underline{CH_2}$—CH$_2$—CH$_2$—CH$_3$ 0.90-1.90 ppm: m: 17H: cyclohexyl-+—CH$_2$—CH$_3$+—CH$_2$—CH$_2$—CH$_3$ 0.80 ppm: t: 3H: —CH$_3$ 0.60 ppm: t: 3H: —C$\underline{H_3}$

EXAMPLE 62

(R,S)-2-n-Butyl-4-cyclohexyl-4-methyl-1-[(2'-(tetrazol-5-yl)biphenyl-4-yl)methyl]-2-imidazolin-5-one A) 4-Methyl-2'-(tetrazol-5-yl)biphenyl 2'-Cyano-4-methylbiphenyl is prepared according to European patent application 324 377.

2 g of this compound are placed in a round-bottomed flask in the presence of 4 g of tributyltin azide and 20 ml of xylene and the mixture is refluxed for 110 hours. After it has returned to RT, the reaction medium is diluted with toluene and the organic phase is then extracted 3 times with 50 ml of 1N sodium hydroxide solution. The aqueous phases are combined, washed with ether and then cooled in a bath of iced water and acidified to pH 1-2 by the addition of concentrated hydrochloric acid. The precipitate formed is filtered off, washed with water and dried under vacuum over phosphorus pentoxide to give 2.18 g of the expected product.

M.p.=146°-148° C. after recrystallization from ethyl acetate.

B) 4-Methyl-2'-(triphenylmethyltetrazol-5-yl)biphenyl 5.46 g of the compound obtained in step A, 6.9 g of trityl chloride, 100 ml of DCM and 4 ml of triethylamine are mixed in a round-bottomed flask. The medium is refluxed for 4 hours and then evaporated. The residue is taken up in ethyl acetate and washed with water, a 3% solution of potassium hydrogensulfate, 1N sodium hydroxide solution, water and then a saturated solution of sodium chloride. It is dried over sodium sulfate, filtered and evaporated to give 11 g of the expected product.

M.p.=161°-164° C.

C) 4-Bromomethyl-2'-(triphenylmethyltetrazol-5-yl)biphenyl

A mixture containing 11 g of the compound prepared in step B, 140 ml of carbon tetrachloride, 4.12 g of NBS and 0.4 g of benzoyl peroxide is refluxed for 3 hours. After it has returned to RT, it is filtered and the filtrate is then evaporated. The residue is taken up in 30 ml of isopropyl ether. The precipitate formed is filtered off and then dried under vacuum.

The product obtained is used as such in the next step.

D) (R,S)-2-n-Butyl-4-cyclohexyl-4-methyl-1-[(2'-(triphenylmethyltetrazol-5-yl)biphenyl-4-yl)methyl]-2-imidazolin-5-one 394 mg of sodium hydride as an 80% dispersion in oil are suspended in 100 ml of anhydrous DMF under nitrogen, 1.71 g of 2-n-butyl-4-cyclohexyl-4-methyl-2-imidazolin-5-one in 10 ml of anhydrous DMF, prepared in Example 59, step E), are added gradually, with stirring, and the mixture is stirred for 30 minutes. 4.86 g of the compound prepared in step C) are added and the mixture is stirred for 3 hours at RT. It is evaporated to dryness, the residue is then taken up in 60 ml of ethyl acetate and the medium is filtered and evaporated to dryness. The oil obtained is chromatographed on silica using an ethyl acetate/hexane mixture (1/3; v/v) as the eluent. After evaporation of the solvents, 3.45 g of the expected product are obtained in the form of a solid foam.

NMR (CDCl$_3$): 0.9 ppm: m: 3H: —CH$_2$—CH$_2$—CH$_2$—C$\underline{H_3}$ 1-1.8 ppm: m: 18H: 4-methyl+4-cyclohexyl+$\underline{CH_2}$—CH$_2$—CH$_2$—CH$_3$ 2.35 ppm: distorted t: 2H: C$\underline{H_2}$—CH$_2$—CH$_2$—CH$_3$ 4.5 ppm: s: 2H: N—CH$_2$—C$_6$H$_4$— 6.70-8 ppm: m: 23H: aromatic protons E) (R,S)-2-n-Butyl-4-cyclohexyl-4-methyl-1-[(2'-(tetrazol-5-yl)biphenyl-4-yl)methyl]-2-imidazolin-5-one 3.38 g of the compound prepared in step D) are dissolved in a mixture of 40 ml of methanol and 20 ml of THF. 3.5 ml of 4N hydrochloric acid are added and the mixture is stirred for 3 hours at RT. After evaporation to dryness, the residue is taken up in 10 ml of 2N sodium hydroxide solution and 10 ml of ether and the mixture is then stirred until a solution is formed. The aqueous phase is extracted twice with ether. The aqueous phase is acidified to pH 6 with dilute hydrochloric acid and then extracted 3 times with ethyl acetate and the extracts are dried over sodium sulfate and evaporated to dryness to give 1.72 g of the expected product in the form of a white solid foam.

NMR (CDCl$_3$): 0.9 ppm: t: 3H: CH$_2$—CH$_2$—CH$_2$—C$\underline{H_3}$ 0.95-2.7 ppm: m: 18H: 4-cyclohexyl+4-methyl+—CH$_2$—CH$_2$—CH$_2$—CH$_3$ 2.1 ppm: t: 2H: —C$\underline{H_2}$—CH$_2$—CH$_2$—CH$_3$ 4.4-4.7 ppm: AB system: 2H: N—CH$_2$—C$_6$H$_4$— 6.95-7.1 ppm: q: 4H: aromatic protons 7.3-7.6 ppm: m: 3H: aromatic protons 7.8; d: 1H: aromatic protons

EXAMPLE 63

2-n-Butyl-4-cyclohexyl-4-methyl-1-[(2'-(tetrazol-5-yl)biphenyl-4-yl)methyl]-2-imidazolin-5-one, levorotatory A) 5-Methyl-5-phenylhydantoin 30 g of acetophenone diluted in 250 ml of 95° alcohol are added over 30 minutes to a mixture of 18.35 g of sodium cyanide and 125 g of ammonium bicarbonate in 250 ml of water and the reaction medium is heated at 60°-65° C. for 22 hours, with stirring. It is concentrated to half its volume under vacuum and the solid which has precipitated is filtered off, washed with water and ether and then dried under vacuum to give 38 g of a white solid, which is identified by IR.

M.p. = 190°–192° C.

B) (R,S)-2-Amino-2-phenylpropionic acid 20 g of the compound prepared in the previous step are added to a mixture of 75 g of barium hydroxide octahydrate and 500 ml of water and the reaction medium is then heated at 160° C. for 5 hours in a steel tube. It is saturated with dry ice and the precipitate is then filtered off. The filtrate is concentrated under vacuum and the white solid formed is taken up in acetone, filtered off, washed with acetone and ether and then dried to give 15.3 g of the expected acid.

M.p. = 260°–265° C. (with decomposition).

C) Ethyl ester of (R,S)-2-amino-2-phenylpropionic acid

Using a spatula, 24 g of the acid prepared in the previous step are added to a solution of 80 g of gaseous hydrochloric acid in 210 ml of absolute ethanol, with stirring, and the mixture is refluxed for 6 and a half hours. It is concentrated under vacuum, the residue is taken up in 600 ml of ethyl acetate and 100 ml of water, and 2N sodium hydroxide solution is added until the pH is 9. The organic phase is decanted, washed with water and with a saturated solution of sodium chloride, dried over sodium sulfate and then concentrated under vacuum to give 25.5 g of the expected product in the form of an oil. Identification by IR.

D) Dextrorotatory ethyl ester of 2-amino-2-phenylpropionic acid

The enantiomers of the ester prepared in the previous step are separated by the method described by Y. Sugi and S. Mitsui in Bull. Chem. Soc. Japan, 1969, 42, 2984–2988. 19.8 g of (L)(+)-tartaric acid are added to the 25.5 g of ester obtained in step C, diluted in 210 ml of absolute ethanol. The mixture is heated to 60° C. to give a total solution, which is then left to stand at RT for 4 hours. The precipitate formed is filtered off, then rinsed with twice 70 ml of absolute alcohol and then redissolved in 200 ml of alcohol at the boil and the solution is then left to stand at RT for 72 hours. The acicular crystals formed are filtered off, rinsed twice with 30 ml of alcohol and then dried under vacuum to give 11.9 g of the tartaric acid salt of the expected dextrorotatory ester.

M.p. = 172°–173° C. $[\alpha]_D = +44.5°$ (C=1, water).

The remaining alcoholic solution is enriched in the tartaric acid salt of the levorotatory ester.

6.1 g of the tartaric acid salt of the dextrorotatory ester are taken up in 30 ml of water and then 200 ml of ethyl acetate, and 5N sodium hydroxide solution is added until the pH is 9. The organic phase is decanted, washed with water and a saturated solution of sodium chloride, dried over sodium sulfate and then concentrated under vacuum to give 3.33 g of the expected product in the form of an oil.

$[\alpha]_D = +24°$ (C=2, ethanol). Identification by NMR.

E) Dextrorotatory ethyl ester of 2-amino-2-cyclohexylpropionic acid 3.30 g of the dextrorotatory ester obtained in the previous step are diluted in 120 ml of acetic acid; 1.5 g of platinum oxide are added and the mixture is then hydrogenated at atmospheric pressure. After hydrogenation for 40 hours, the reaction medium is filtered and then concentrated under vacuum. The residue is taken up in ether/water mixture and 6N hydrochloric acid is added until the pH is 2. The organic phase is separated from the aqueous phase. Ethyl acetate is added, followed by 5N sodium hydroxide solution until the pH is 9.5. The organic phase is decanted, washed with water and a saturated solution of sodium chloride, dried over sodium sulfate and then concentrated under vacuum to give 3.10 g of the expected product.

$[\alpha]_D = +18°$ (C=2, ethanol). Literature: W. A. Bonner et al., J. Amer. Chem. Soc., 1956, 78, 3218–3221.

Identification by NMR.

F) 2-n-Butyl-4-cyclohexyl-4-methyl-2-imidazolin-5-one, levorotatory

A mixture containing 3 g of the dextrorotatory ester obtained in the previous step, 4.7 g of ethyl valerimidate and 8 drops of acetic acid in 15 ml of xylene is brought to the reflux point, with stirring.

After refluxing for 7 hours, the reaction medium is concentrated under vacuum. The residue is chromatographed on silica using a chloroform/methanol/acetic acid mixture (95/9/3) as the eluent; the fractions containing the product are combined and concentrated under vacuum. The residue is taken up in an ethyl acetate/water mixture and the pH is brought to 9 by the addition of 5N sodium hydroxide solution. The organic phase is decanted, washed with water and a saturated solution of sodium chloride, dried over sodium sulfate and concentrated under vacuum to give an oil, which changes to an amorphous solid.

m = 2.36 g. $[\alpha]_D = -57.2°$ (C=1, chloroform). IR (chloroform): 1720 cm$^{-1}$: C=O 1640 cm$^{-1}$: C=N The IR spectrum confirms the 5-one form of the imidazolinone in solution.

G) 2-n-Butyl-4-cyclohexyl-4-methyl-1-[(2'-(triphenylmethyltetrazol-5-yl)biphenyl-4-yl)methyl]imidazoline-2-one 5, levorotatory This compound is prepared from the product prepared in step F by following the procedure described in Example 62, step D.

Yield: 73%. $[\alpha]_D = -22.8°$ (C=1, chloroform). NMR: superimposable on that of the compound of Example 62, step D.

H) 2-n-Butyl-4-cyclohexyl-4-methyl-1-[(2'-(tetrazol-5-yl)biphenyl-4-yl)methyl]-2-imidazolin-5-one, levorotatory This compound is prepared from the product prepared in step G by following the procedure described in Example 62, step E.

Yield: 85%. $[\alpha]_D = -25.9°$ (C=1, methanol). NMR: superimposable on that of the compound of Example 62, step E.

EXAMPLE 64

2-n-Butyl-4-cyclohexyl-4-methyl-1-[(2'-(tetrazol-5-yl)biphenyl-4-yl)methyl]-2-imidazolin-5-one, dextrorotatory A) Levorotatory ethyl ester of 2-amino-2-phenylpropionic acid The alcoholic solution obtained in Example 63, step D), is concentrated after separation of the crystals of the tartaric acid salt of the dextrorotatory ethyl ester of 2-amino-2-phenylpropionic acid. The solid residue is taken up in 150 ml of water and 600 ml of ethyl acetate and the pH is brought to 9 by the addition of 5N sodium hydroxide solution. The organic phase is decanted, washed with water and a saturated solution of sodium chloride, dried over sodium sulfate and then concentrated under vacuum to give 20.6 g of the ester enriched in the levorotatory form.

15.9 g of (D)(−)-tartaric acid are added to 20.5 g of this ester diluted in 200 ml of absolute ethanol, and a solution is formed at the boiling point of the alcohol. After 5 hours at RT, the acicular crystals formed are filtered off, washed twice with 50 ml of absolute alcohol and then dried under vacuum to give 16.3 g of the tartaric acid salt of the expected product.

M.p.=172°–173° C. $[\alpha]_D = -45.2°$ (C=1, water).

6 g of the salt obtained are taken up in 50 ml of water and 200 ml of ethyl acetate and the pH is brought to 9.5 by the addition of 5N sodium hydroxide solution. The organic phase is decanted, washed with water and a saturated solution of sodium chloride and then dried over sodium sulfate and concentrated under vacuum to give 3.31 g of the expected product in the form of an oil, which is identified by NMR.

$[\alpha]_D = -25.5°$ (C=2, ethanol).

B) Levorotatory ethyl ester of 2-amino-2-cyclohexyl-propionic acid

The procedure of Example 63, step E), is followed to give 3.20 g of the expected product from 3.30 g of the compound of step A.

$[\alpha]_D = -19.2°$ (C=1, ethanol).

C) 2-n-Butyl-4-cyclohexyl-4-methyl-2-imidazolin-5-one, dextrorotatory

The procedure of Example 63, step F), is followed.

$[\alpha]_D = +56.9°$ (C=1, chloroform).

The NMR and IR spectra are superimposable on those of the levorotatory isomer prepared in Example 63, step F).

D) 2-n-Butyl-4-cyclohexyl-4-methyl-1-[(2'-(triphenylmethyltetrazol-5-yl)biphenyl-4-yl)methyl]-2-imidazolin-5-one, dextrorotatory The procedure described in Example 63, step G), is followed to give 2.3 g of the expected product in the form of a white solid from 1.1 g of the compound prepared in step C.

$[\alpha]_D = -23.8°$ (C=1, methanol) and NMR spectrum superimposable on that of the compound prepared in Example 62, step D.

E) 2-n-Butyl-4-cyclohexyl-4-methyl-1-[(2'-(tetrazol-5-yl)biphenyl-4-yl)methyl]-2-imidazolin-5-one, dextrorotatory The procedure described in Example 64, step H, is followed to give 1.1 g of the expected product in the form of a white solid from 2.15 g of the compound prepared in step D.

$[\alpha]_D = +27.1°$ (C=1, methanol).

The NMR spectrum is superimposable on that of the compound prepared in Example 62.

Likewise, the following compounds according to the invention were prepared according to the procedure described in Example 61;

EXAMPLE 65

(R,S)-2-n-Butyl-1-[(2'-carboxybiphenyl-4-yl)methyl]-4-cyclopropyl-4-methyl-2-imidazolin-5-one trifluoroacetate M.p.=149°–150° C. NMR: 7.05–7.80 ppm: m: 8H: aromatic protons 4.70 ppm: s: 2H: N—C$\underline{H}_2$—C$_6$H$_4$— 2.45 ppm: t: 2H: C$\underline{H}_2$—CH$_2$—CH$_2$—C$\underline{H}_3$ 1.05–1.45 ppm: m+s: 8H: —C$\underline{H}_2$—C$\underline{H}_2$—C$\underline{H}_2$—CH$_3$+CH$_3$ in the 4 position+cyclopropane CH 0.70 ppm: t: 3H: CH$_3$—(CH$_2$)$_3$— 0.05–0.45 ppm: m: 4H: 2 cyclopropane C$\underline{H}_2$

EXAMPLE 66

(R,S)-2-n-Butyl-1-[(2'-carboxybiphenyl-4-yl)methyl]-4,4-dicyclopropyl-2-imidazolin-5-one trifluoroacetate M.p.=132°–134° C. Mass spectrum: MH+: 431 NMR: 7.15–7.80 ppm: m: 8H: aromatic protons 4.75 ppm: s: 2H: N—C$\underline{H}_2$—C$_6$H$_4$— 2.50 ppm: t: 2H: C$\underline{H}_2$—CH$_2$—CH$_2$—CH$_3$ 1.1–1.60 ppm: m: 6H: C$\underline{H}_2$—C$\underline{H}_2$—C$\underline{H}_2$—CH$_3$+2 cyclopropane CH 0.80 ppm: t: 3H: (C$\underline{H}_2$)$_3$—CH$_3$ 0.10–0.80 ppm: m: 8H: 4 cyclopropane C$\underline{H}_2$

EXAMPLE 67

(R,S)-2-n-Butyl-1-[(2'-carboxybiphenyl-4-yl)methyl]-4-cyclopentyl-4-methyl-2-imidazolin-5-one trifluoroacetate M.p.=104°–107° C. NMR: 7.20–7.80 ppm: m: 8H: aromatic protons 4.85 ppm: AB system: 2H: N—CH$_2$—C$_6$H$_4$— 2.75 ppm: distorted t: 2H: C$\underline{H}_2$—CH$_2$—C$\underline{H}_2$—CH$_3$ 2.20–1.00 ppm: m+s: 16H: cyclopentane+CH$_3$ in the 4 position+—C$\underline{H}_2$—C$\underline{H}_2$—CH$_3$ 0.80 ppm: t: 3H: CH$_3$—(CH$_2$)$_3$—

What is claimed is:

1. A compound of the formula $$\begin{array}{c} R_4 \\ R_5 \!\!-\!\!\!\!\!\!\diagup\!\!\!-\!\!(CH_2)_t \\ \quad\quad\quad\quad\backslash \\ z(CH_2) \quad\quad N \\ \quad\diagdown\!\!\!\diagup\!\!\!\!\searrow \\ X \quad\quad N \quad R_3 \\ \quad\quad | \\ \quad\quad H \end{array} \quad (II)$$

in which:

R$_3$ is a hydrogen, a C$_1$–C$_6$ alkyl which is unsubstituted or substituted by one or more halogen atoms, a C$_2$–C$_6$ alkenyl, a C$_3$–C$_7$ cycloalkyl, a phenyl, a phenylalkyl in which the alkyl is C$_1$–C$_3$, or a phenylalkenyl in which the alkenyl is C$_2$–C$_3$, said phenyl groups being unsubstituted or monosubstituted or polysubstituted by a halogen atom, a C$_1$–C$_4$ alkyl, a C$_1$–C$_4$ halogenoalkyl, a C$_1$–C$_4$ polyhalogenoalkyl, a hydroxyl or a C$_1$–C$_4$ alkoxy; and either R$_4$ and R$_5$ are each independently a C$_1$–C$_6$ alkyl, a phenyl or a phenylalkyl in which the alkyl is C$_1$–C$_3$, said alkyl, phenyl and phenylalkyl groups being unsubstituted or substituted by one or more halogen atoms or by a group selected from a C$_1$–C$_4$ perfluoroalkyl, a hydroxyl and a C$_1$–C$_4$ alkoxy;

or R$_4$ and R$_5$ together form a group of the formula =CR$_7$R$_8$, in which R$_7$ is hydrogen, a C$_1$–C$_4$ alkyl or a phenyl and R$_8$ is a C$_1$–C$_4$ alkyl or a phenyl;

or else R$_4$ and R$_5$ together are either a group of the formula (CH$_2$)$_n$ or a group of the formula (CH$_2$)$_p$Y—(CH$_2$)$_q$, in which Y is either an oxygen atom, or a sulfur atom, or a carbon atom substituted by a C$_1$–C$_4$ alkyl group, a phenyl or a phenylalkyl in which the alkyl is C$_1$–C$_3$, or a group N—R$_6$, in which R$_6$ is a hydrogen, a C$_1$–C$_4$ alkyl, a phenylalkyl in which the alkyl is C$_1$–C$_3$, a C$_1$–C$_4$ alkylcarbonyl, a C$_1$–C$_4$ halogenoalkylcarbonyl, a C$_1$–C$_4$ polyhalogenoalkylcarbonyl, a benzoyl, an alpha-aminoacyl or an N-protecting group, or R$_4$ and R$_5$, together with the carbon atom to which they are bonded, form an indane or an adamantane;
p+q=m;
n is an integer between 2 and 11;
m is an integer between 2 and 5;
X is an oxygen atom or sulfur atom; and
z and t are zero or one is zero and the other is one;
with the limitation that
if z and t are zero and X is an oxygen atom, $R_4$ and $R_5$ are other than
a $C_1$–$C_6$ alkyl, a phenyl or a phenylalkyl in which the alkyl is $C_1$–$C_3$, said alkyl, phenyl and phenylalkyl groups being unsubstituted or substituted by one or more halogen atoms or by a group selected from a $C_1$–$C_4$ perfluoroalkyl, a hydroxyl and a $C_1$–$C_4$ alkoxy;
or $R_4$ and $R_5$ together are other than a group N—$R_6$ in which $R_6$ is a hydrogen, a $C_1$–$C_4$ alkyl or a phenylalkyl in which the alkyl is $C_1$–$C_3$; and n is other than 6; or
when $R_3$ represents a substituted phenyl group, $R_4$ and $R_5$ together are other than a $(CH_2)_n$ group in which n is between 3 and 5;
and
if z=1 and $R_3$ is a phenyl, $R_4$ and $R_5$ are each other than a methyl; or
$R_4$ is a $C_1$–$C_6$ alkyl which is unsubstituted or substituted by one or more halogen atoms; and
$R_5$ is a cycloalkyl or a cycloalkylmethyl, said cycloalkyl being $C_3$–$C_7$, which is unsubstituted or substituted by one or more halogen atoms;
or $R_4$ and $R_5$ are each a cyclopropyl;
X is an oxygen atom or sulfur atom; and
z and t are zero or one is zero and the other is one.

2. A compound according to claim 1 of the formula

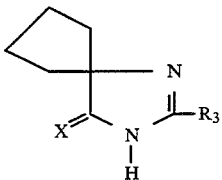

(II'$_a$)

in which X is an oxygen atom or a sulfur atom and $R_3$ is a hydrogen, a $C_1$–$C_6$ alkyl which is unsubstituted or substituted by one or more halogen atoms, a $C_2$–$C_6$ alkenyl, a $C_3$–$C_7$ cycloalkyl, a phenyl, a phenylalkyl in which the alkyl is $C_1$–$C_3$, or a phenylalkenyl in which the alkenyl is $C_2$–$C_3$, said phenyl groups being unsubstituted or monosubstituted or polysubstituted by a halogen atom, a $C_1$–$C_4$ alkyl, a $C_1$–$C_4$ halogenoalkyl, a $C_1$–$C_4$ polyhalogenoalkyl, a hydroxyl or a $C_1$–$C_4$ alkoxy; with the proviso that $R_3$ is other than a substituted phenyl group when X is oxygen.

3. A compound according to claim 1 of the formula

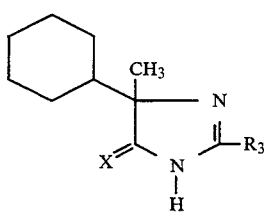

(II'$_b$)

in which X and $R_3$ are as defined for (II) in claim 1.

4. A compound according to claim 1 of the formula

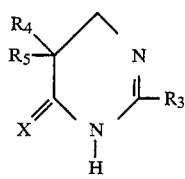

(II'')

in which $R_3$, $R_4$, $R_5$ and X are as defined above for (II) in claim 1.

5. A compound according to claim 1 of the formula

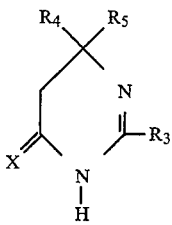

(II''')

in which X, $R_3$, $R_4$ and $R_5$ are as defined for (II) in claim 1.

6. A method of preparing a compound of formula (II):

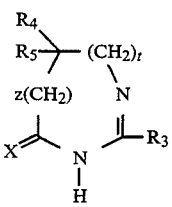

(II)

which method comprises:
(I) reacting a compound of formula 14:

$R_3$—T    14 with a compound of formula 13:

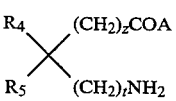

13 wherein:
$R_3$ is a hydrogen, a $C_1$–$C_6$ alkyl which is unsubstituted or substituted by one or more halogen atoms, a $C_2$–$C_6$ alkenyl, a $C_3$–$C_7$ cycloalkyl, a phenyl, a phenyl($C_1$–$C_3$)alkyl, or a phenyl($C_2$–$C_3$)alkenyl, said phenyl groups being unsubstituted or monosubstituted or polysubstituted by a halogen atom, a $C_1$–$C_4$ alkyl, a $C_1$–$C_4$ halogenoalkyl, a $C_1$–$C_4$ polyhalogenoalkyl, a hydroxyl or a $C_1$–$C_4$ alkoxy; and $R_4$ and $R_5$ are each independently a $C_1$–$C_6$ alkyl, a phenyl or a phenyl($C_1$–$C_3$)alkyl, said alkyl, phenyl and phenylalkyl groups being unsubstituted or substituted by one or more halogen atoms or by a $C_1$–$C_4$ perfluoroalkyl, a hydroxyl or a $C_1$–$C_4$ alkoxy; or R4 and R5 together form a group of the formula =CR7R8, in which R7 is hydrogen, a C1-C4 alkyl or a phenyl and R8 is a C1-C4 alkyl or a phenyl; or R4 and R5 together are either a group of the formula (CH2)n or a group of the formula (CH2)pY—(CH2)q, in which Y is an oxygen atom, a sulfur atom, or a carbon atom substituted by a C1-C4 alkyl group, a phenyl or a phenyl(C1-C3)alkyl, or a group N—R6, in which R6 is a hydrogen, a C1-C4 alkyl, a phenyl(C1-C3)alkyl, a C1-C4 alkylcarbonyl, a C1-C4 halogenoalkylcarbonyl, a C1-C4 polyhalogenalkylcarbonyl, a benzoyl, an alpha-aminoacyl or an N-protecting group; or R4 and R5, together with the carbon atom to which they are bonded, form an indane or an adamantane;

p+q=m;
n is an integer between 2 and 11;
m is an integer between 2 and 5;
X is an oxygen atom or sulfur atom; and
z and t are zero and one is zero and the other is one; with the limitations that:

if z and t are zero and X is an oxygen atom, R4 and R5 are other than a C1-C6 alkyl, a phenyl or a phenyl(C1-C3)alkyl, said alkyl, phenyl and phenylalkyl groups being unsubstituted or substituted by one or more halogen atoms or by a C1-C4 perfluoroalkyl, a hydroxyl or a C1-C4 alkoxy;

or R4 and R5 together are other than a group N—R6 in which R6 is a hydrogen, a C1-C4 alkyl or a phenyl(C1-C3)alkyl; and n is other than 6; or when R3 represents a substituted phenyl group, R4 and R5 together are other than a (CH2)n group in which n is between 3 and 5; and if z=1 and R3 is a phenyl, R4 and R5 are each other than a methyl; or R4 is a C1-C6 alkyl which is unsubstituted or substituted by one or more halogen atoms; and R5 is a cycloalkyl or a (C3-C7) cycloalkylmethyl, which is unsubstituted or substituted by one or more halogen atoms; or R4 and R5 are each a cyclopropyl;

T is C(OR)3, HN=C—OR or COHal, wherein R is C1-C4 alkyl and Hal is a halogen atom;

A is an OH group, an NH2 group or a group R', wherein R' is hydrogen or a C1-C4 alkyl group; and (II) optionally treating the resulting compounds in which X=O with Lawesson's reagent (2,4-bis(4-methoxyphenyl)-1,3-dithia-2,4-diphosphate disulfide) to transform them into compounds of formula (II) in which X=S.

7. A method as claimed in claim 6 of preparing a compound of formula (II'a):

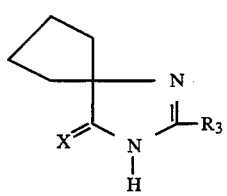

(II'a)

in which X is an oxygen atom or a sulfur atom and R3 is a hydrogen, a C1-C6 alkyl which is unsubstituted or substituted by one or more halogen atoms, a C2-C6 alkenyl, a C3-C7 cycloalkyl, a phenyl, a phenyl(C1-C3)alkyl, a phenyl(C2-C3)alkenyl, said phenyl groups being unsubstituted or monosubstituted or polysubstituted by a halogen atom, a C1-C4 alkyl, a C1-C4 halogenoalkyl, a C1-C4 polyhalogenoalkyl, a hydroxyl or a C1-C4 alkoxy; with the proviso that R3 is other than a substituted phenyl group when X is oxygen.

8. A method as claimed in claim 6 of preparing a compound of formula (II'b)

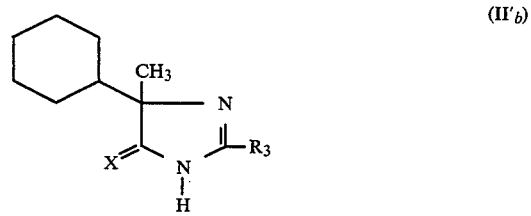

(II'b)

in which
X is an oxygen atom or a sulfur atom; and
R3 is a hydrogen, a C1-C6 alkyl which is unsubstituted or substituted by one or more halogen atoms, a C2-C6 alkenyl, a C3-C7 cycloalkyl, a phenyl, a phenyl(C1-C3)alkyl, a phenyl(C2-C3)alkenyl, said phenyl groups being unsubstituted or monosubstituted or polysubstituted by a halogen atom, a C1-C4 alkyl, a C1-C4 halogenoalkyl, a C1-C4 polyhalogenoalkyl, a hydroxyl or a C1-C4 alkoxy.

9. A method as claimed in claim 6 of preparing a compound of formula (II")

(II")

in which R3, R4, R5 and X are as defined in claim 6.

10. A method as claimed in claim 6 of preparing a compound of formula (II'")

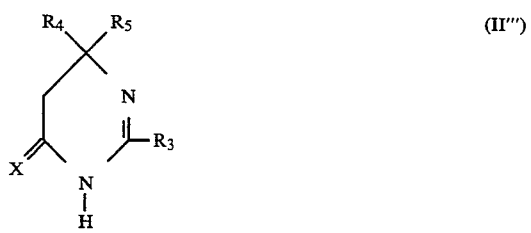

(II'")

in which R3, R4, R5, and X are as defined in claim 6.

11. A method according to claim 6 wherein Hal is chlorine.

12. A method according to claim 7 wherein Hal is chlorine.

13. A method according to claim 8 wherein Hal is chlorine.

14. A method according to claim 9 wherein Hal is chlorine.

15. A method according to claim 10 wherein Hal is chlorine.

16. A compound according to claim 2 wherein R3 is n-butyl and X is oxygen.

* * * * *

UNITED STATES PATENT AND TRADEMARK OFFICE
CERTIFICATE OF CORRECTION

PATENT NO. : 5,352,788

DATED : October 4, 1994

INVENTOR(S) : Claude BERNHART et al.

It is certified that error appears in the above-indentified patent and that said Letters Patent is hereby corrected as shown below:

Column 1, line 58, delete "N-cyanoacetamide" and insert --N-cyanocarbamoyl--;

line 59, delete "hydroxyacetamide" and insert --hydroxycarbamoyl--;

line 60, delete "yl)acetamide" and insert --yl)carbamoyl--.

Column 9, line 37, delete "yl)acetamide" and insert --yl)carbamoyl--;

line 40, delete "N-hydroxyacetamide, N-cyanoacetamide" and insert --N-hydroxycarbamoyl, N-cyanocarbamoyl--.

Column 32, line 27, delete "cyanocarboxamidebiphenyl" and insert --cyanocarbamoylbiphenyl--.

Column 33, line 59, delete "Cyanocarboxamidebiphenyl" and insert --Cyanocarbamoylbiphenyl--.

Column 34, line 20, delete "ylacetamide" and insert therefor --ylcarbamoyl--.

Signed and Sealed this

Eighth Day of July, 1997

Attest:

*Attesting Officer*

BRUCE LEHMAN

*Commissioner of Patents and Trademarks*